US011135202B2

(12) United States Patent
Rossignol et al.

(10) Patent No.: US 11,135,202 B2
(45) Date of Patent: Oct. 5, 2021

(54) THIAZOLIDE COMPOUNDS FOR TREATING VIRAL INFECTIONS

(71) Applicant: Romark Laboratories L.C., Tampa, FL (US)

(72) Inventors: Jean-Francois Rossignol, St. Petersburg, FL (US); Maria Gabriella Santoro, Rome (IT)

(73) Assignee: Romark Laboratories L.C., Tampa, FL (US)

( * ) Notice: Subject to any disclaimer, the term of this patent is extended or adjusted under 35 U.S.C. 154(b) by 0 days.

(21) Appl. No.: 15/474,267

(22) Filed: Mar. 30, 2017

(65) Prior Publication Data

US 2017/0281603 A1 Oct. 5, 2017

Related U.S. Application Data

(60) Provisional application No. 62/316,463, filed on Mar. 31, 2016.

(51) Int. Cl.
*A61K 31/426* (2006.01)
*A61K 45/06* (2006.01)

(52) U.S. Cl.
CPC .......... *A61K 31/426* (2013.01); *A61K 45/06* (2013.01)

(58) Field of Classification Search
CPC .................................................. A61K 31/426
See application file for complete search history.

(56) References Cited

U.S. PATENT DOCUMENTS

| | | |
|---|---|---|
| 3,950,351 A | 4/1976 | Rossignol et al. |
| 5,387,598 A | 2/1995 | Rossignol |
| 5,856,348 A | 1/1999 | Rossignol |
| 5,859,038 A | 1/1999 | Rossignol |
| 5,886,013 A | 3/1999 | Rossignol |
| 5,935,591 A | 8/1999 | Rossignol et al. |
| 5,965,590 A | 10/1999 | Rossignol |
| 5,968,961 A | 10/1999 | Rossignol |
| 6,020,353 A | 2/2000 | Rossignol |
| 6,117,894 A | 9/2000 | Rossignol |
| 7,285,567 B2 | 10/2007 | Rossignol |
| 7,550,493 B2 | 6/2009 | Rossignol |
| 7,645,783 B2 | 1/2010 | Rossignol |
| 8,124,632 B2 | 2/2012 | Rossignol et al. |
| 8,362,018 B2 * | 1/2013 | MacLeod ............ C07D 487/04 514/249 |
| 8,524,278 B2 | 9/2013 | Rossignol et al. |
| 8,633,230 B2 | 1/2014 | Rossignol |
| 8,772,502 B2 | 7/2014 | Semple et al. |
| 8,796,273 B2 * | 8/2014 | Neyts et al. ......... A61K 31/501 514/252.03 |
| 8,846,727 B2 | 9/2014 | Rossignol et al. |
| 8,895,752 B2 | 11/2014 | Rossignol et al. |
| 9,023,877 B2 | 5/2015 | Rossignol et al. |
| 9,107,913 B2 | 8/2015 | Rossignol |
| 9,126,992 B2 | 9/2015 | Rossignol et al. |
| 9,351,937 B2 | 5/2016 | Rossignol et al. |
| 2009/0036467 A1 | 2/2009 | Rossignol et al. |
| 2010/0330173 A1 | 12/2010 | Rossignol et al. |
| 2012/0294831 A1 | 11/2012 | Rossignol |
| 2014/0065215 A1 | 3/2014 | Rossignol et al. |
| 2015/0105341 A1* | 4/2015 | Beigelman et al. ..... C07H 19/20 514/252.03 |
| 2015/0250768 A1 | 9/2015 | Rossignol et al. |
| 2016/0243087 A1 | 8/2016 | Rossignol et al. |

FOREIGN PATENT DOCUMENTS

| | | | |
|---|---|---|---|
| JP | 2011-057695 A | 3/2011 | |
| WO | WO-2004/091519 A2 | 10/2004 | |
| WO | WO 2006/042195 A1 | 4/2006 | |
| WO | WO-2016/044656 A1 * | 3/2016 | ............. A61K 38/46 |
| WO | WO 2016/077420 A1 | 5/2016 | |

OTHER PUBLICATIONS

Haffizulla et al., Lancet Infectious Diseases, Jul. 2014, 14(7), pp. 609-618 (Year: 2014).*

Piacentini et al., "Nitazoxanide Potently Inhibits Paramyxovirus Replication in vitro: Effect on Viral Glycoproteins Maturation," Societa Italiana Di Microbiolgia—43rd National Congress of the Italian Society of Microbiology, Sep. 27, 2015, p. 66, Poster Abstract P012, XP055370452, http://www.societasim.it/documenti/sim2015-atti.pdf, retrieved on May 9, 2017.

Rossignol et al. "Activity of Thiazolides Against Other Respiratory Viruses than Influenza," Influenza and Other Respiratory Virus Infections: Advances in Clinical Management, Jun. 6, 2014, p. 81, Poster Abstract P54, XP055370352, https://isirv.org/site/images/stories/avg/documents/intranet/Tokyo/programe-abstract_book.pdf, retrieved on May 8, 2017.

Santoro et al., "Thiazolides: A New Class of Broad-Spectrum Antiviral Drugs Targeting Virus Maturation," Antiviral Research, Mar. 27, 2007, 74(3):A31, XP022002046.

Vigant et al., "Broad-spectrum antivirals against viral fusion," Nature Reviews Microbiology, Jun. 15, 2015, 13(7):426-437, XP055369859.

Lee et al., "Modes of Paramyxovirus Fusion : a Henipavirus perspective, " Trends in Microbiology, Aug. 1, 2011, 19(8) :389-399, XP055370465.

Choppin et al., "The Role of Viral Glycoproteins in Adsorption, Penentration, and Pathogenicity of Viruses," Reviews of Infectious Diseases, Jan.-Feb. 1980, 2(1):40-61, XP9194313.

Piacentini et al., "Thiazolides Inhibit Hendra Virus F Protein Maturation and Intracellular Trafficking in Human Cells," 44th Congresso Nazionale della Societa Italiana Di Microbiologia, Sep. 25, 2016, pp. 123-124, Poster Abstract P094, XP055370447.

(Continued)

*Primary Examiner* — Laura L Stockton

(74) *Attorney, Agent, or Firm* — Foley & Lardner LLP

(57) ABSTRACT

Thiazolide compounds, such as nitazoxanide and/or tizoxanide, may be used against viruses belonging to the Picornaviridae family or the Paramyxoviridae family.

10 Claims, 19 Drawing Sheets

(56) References Cited

OTHER PUBLICATIONS

Bernasconi et al., "The IκB Kinaes Is a Key Factor in Triggering Influenza A Virus-induced Inflammatory Cytokine Production in Airway Epithelial Cells," Journal of Biological Chemistry, Jun. 24, 2005 (online Apr. 18, 2005) 280(25):24127-24134.

La Frazia et al., "Antiviral activity of proteasome inhibitors in herpes simplex virus-1 infection: role of nuclear factor-κB," Antiviral Therapy, 2006, 11(3):995-1004.

Morrison, Trudy G., "Structure and function of a paramyxovirus fusion protein," Biochimica et Biophysica Acta, Jul. 11, 2003, 1614(1):73-84.

Pica et al., "$\Delta^{12}$-Prostaglandin $J_2$ Is a Potent Inhibitor of Influenza A Virus Replication," Antimicrobial Agents and Chemotherapy, Jan. 2000, 44(1):200-204.

Rossi et al., "Anti-inflammatory cyclopentenone prostaglandins are direct inhibitors of IκB kinase," Nature, Jan. 6, 2000, 403:103-108.

Rossignol et al., "Thiazolides, a New Class of Anti-influenza Molecules Targeting Viral Hemagglutinin at the Post-translational Level," Journal of Biological Chemistry, Oct. 23, 2009, 284(43):29798-29808.

Rossignol, Jean-Francois, "Nitazoxanide: A first-in-class broad-spectrum antiviral agent," Antiviral Research, 2014 (online Aug. 7, 2014), 110:94-103.

Rhoden et al., "In Vitro Efficacy of Antiviral Compounds against Enterovirus D68," Antimicrobial Agents and Chemotherapy, Dec. 2015, 59(12):7779-7781.

Scheid et al., "Role of Paramyxovirus Glycoproteins in the Interactions Between Viral and Cell Membranes," Society of General Physiologists Series, Membrane-Membrane Interactions, 1980, 34:119-130.

Belardo et al., "Nitazoxanide, a Novel Potential Anti-Influenza Drug, Acting in Synergism with Neuraminidase Inhibitors," IDSA 2011, Poster Abstract Session: New Approaches to Anti-Viral Therapy, Oct. 22, 2011.

Tsutsumi et al., "Respiratory syncytial virus infection," Japanese Journal of Pediatrics, 2015, 68(12):2509-2513, No English Translation Provided.

* cited by examiner

Figures 4A-B

Detection of the immature form of SeV-F protein in the insoluble fraction of NTZ-treated AGMK cell protein extracts

Figure 10

Nitazoxanide inhibits transport of HeV F glycoprotein to the cell surface pcDNA3 | HeV-F C-FLAG | HeV-F C-FLAG + NTZ

NTZ (10 mg/ml)

HeLa cells

Figures 18 A-B
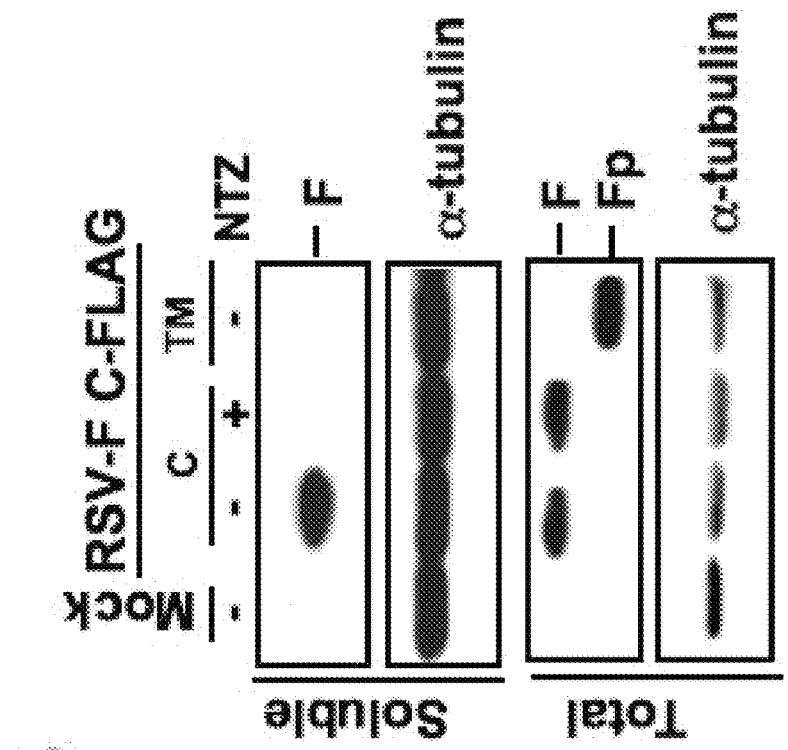
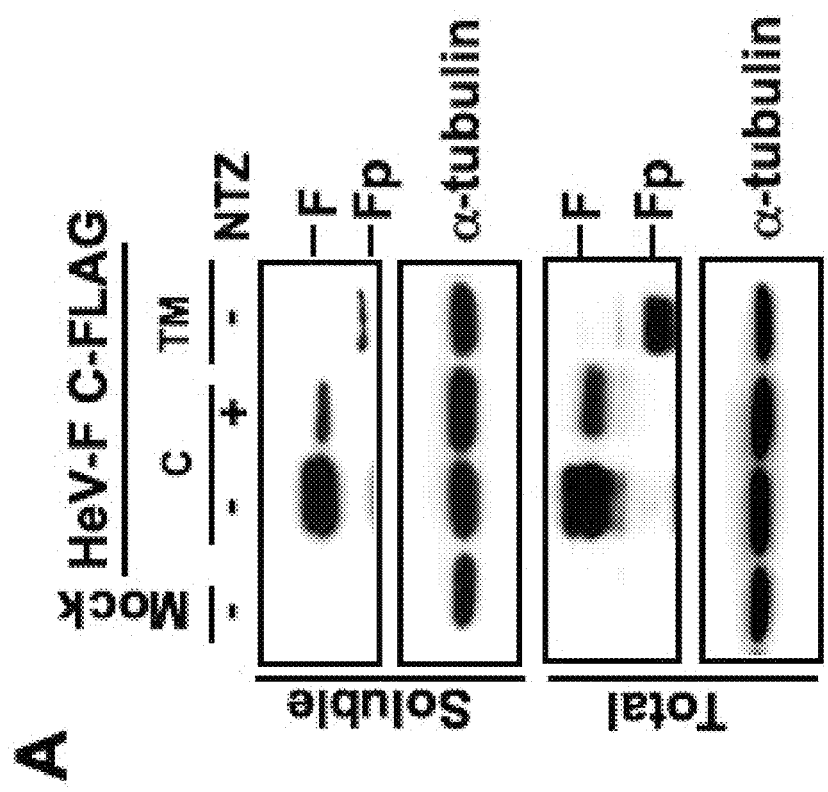

Figures 19 A-B

THIAZOLIDE COMPOUNDS FOR TREATING VIRAL INFECTIONS

PRIORITY

The present application claims priority to U.S. provisional application No. 62/316,463 filed Mar. 31, 2016, which is incorporated herein in its entirety.

FIELD

The present application generally relates to thiazolide compounds and more particularly, to their use in treatment of certain viral infections.

SUMMARY

A method of treating a disease or condition caused by or associated with a virus belonging to the Paramyxoviridae family, comprises administering to a subject in need thereof an effective amount of a pharmaceutical composition comprising at least one of nitazoxanide or tizoxanide or a pharmaceutically acceptable salt thereof, wherein the effective amount is an amount which blocks in the subject the maturation of the F glycoprotein of the virus.

A method of treating a disease or condition caused by or associated with a virus belonging to the Picornaviridae family, comprises administering to a subject in need thereof a therapeutically effective amount of a pharmaceutical composition comprising at least one of nitazoxanide or tizoxanide or a pharmaceutically acceptable salt thereof.

BRIEF DESCRIPTION OF THE DRAWINGS

FIG. 4A presents a plot showing inhibition of Sendai virus as a function nitazoxanide concentration. FIG. 4B presents photographs of control, untreated Sendai virus and Sendai virus treated with nitazoxanide.

FIG. 10 presents photographs, which provide evidence that nitazoxanide inhibits transport of Hendra virus (HeV) F glycoprotein to the cell surface.

NTZ was effective in inhibiting SeV replication at concentrations that were non-toxic for the host cells. NTZ was actually cytoprotective in infected cells. In fact SeV infection (3 PFU/cell) is generally characterized by a massive cytopathic effect, causing a change in cell shape and size, and loss of adhesion (Panel C, SeV). NTZ treatment (10 µg/ml), in addition to inhibiting virus progeny production, was also found to protect AGMK cells from virus-induced damage (Panel C, SeV+NTZ). The information in FIG. 11A-C is similar to the information in FIG. 4A-B.

Figure 5:
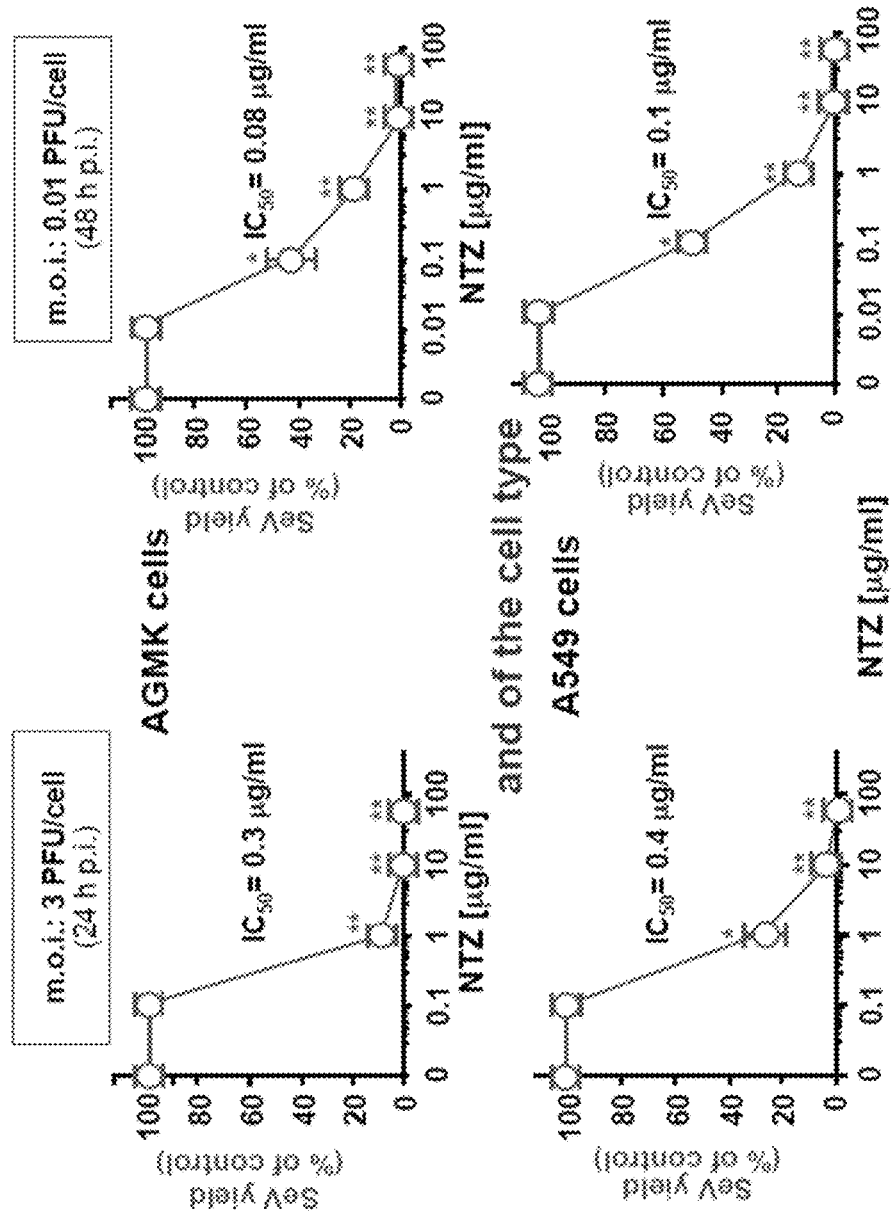
FIG. 5 presents inhibition plots for Sendai virus (SeV) as a function of nitazoxanide concentration for different multiplicities of infection and different type of cells. The data in FIG. 5 show that antiviral activity of nitazoxanide in SeV-infected cells is independent of the multiplicity of infection and the cell type.
Figure 6:
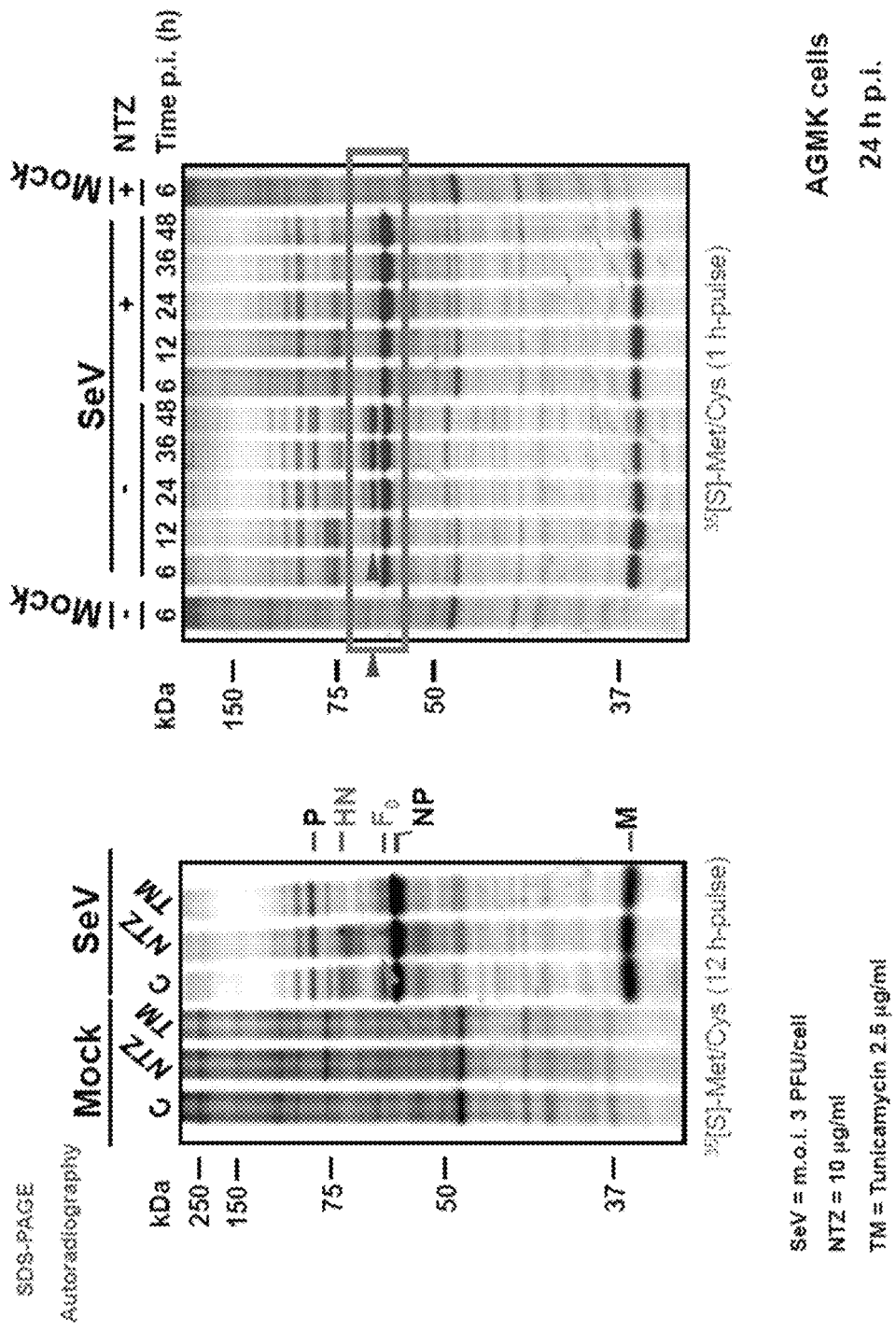
FIG. 6 presents SDS-PAGE data demonstrating effect of nitazoxanide on SeV protein synthesis.
Figure 12:
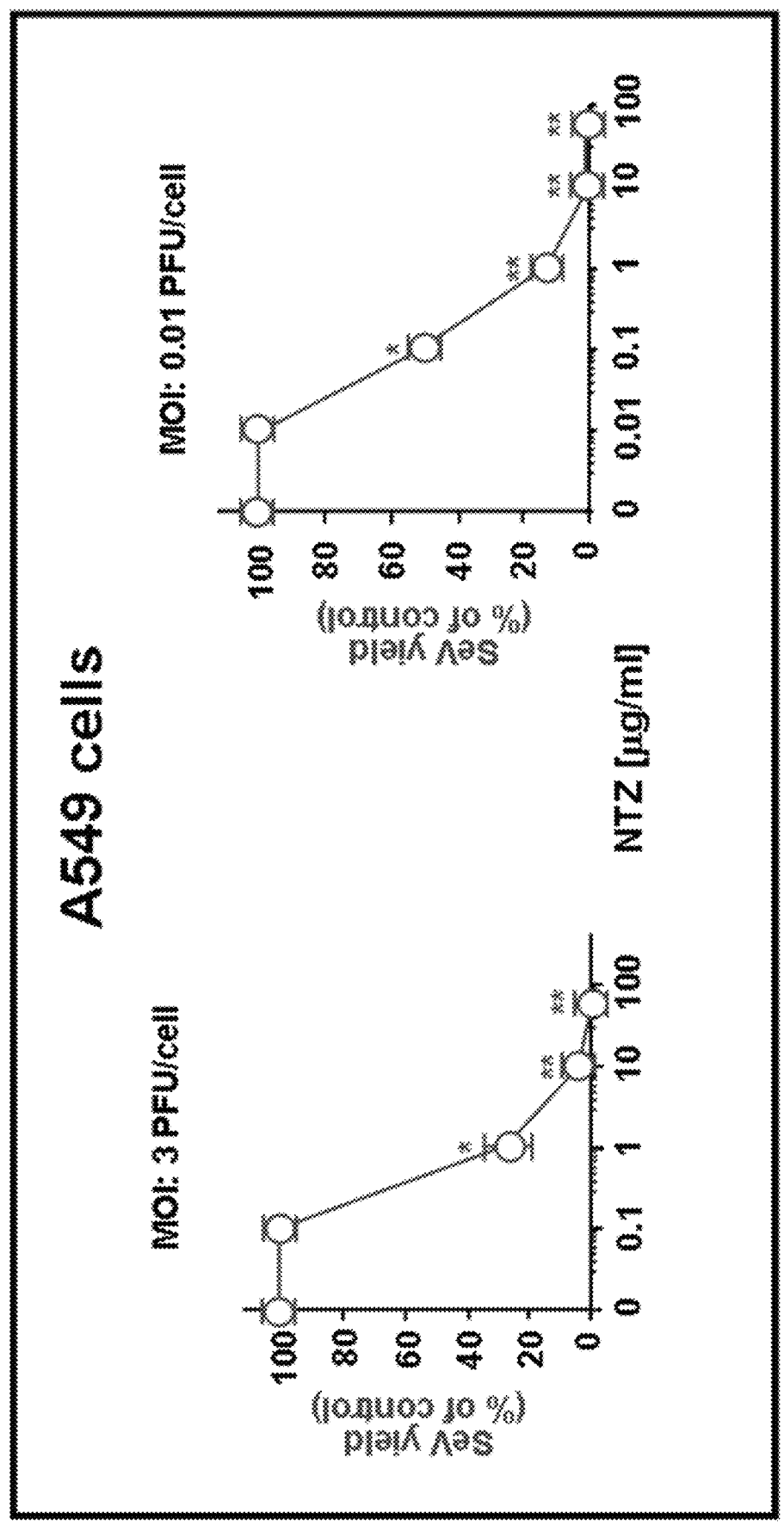
FIG. 12 presents data demonstrating inhibition of SeV parainfluenza virus by nitazoxanide in human alveolar A549 cells. Human alveolar type II-like A549 cells infected with SeV under single-step (3 PFU/cell) and multistep (0.01 PFU/cell) virus growth conditions were treated with different concentrations of NTZ or vehicle immediately after the virus adsorption period. Virus yield (○) was determined at 24 (single-step) or 48 (multistep) h p.i. by HA titration. Virus yield, expressed as percent of untreated control, represents the mean±SD of quadruplicate samples. *=p<0.05; **=p<0.01.

NTZ antiviral activity was independent of the cell type. NTZ was in fact also effective in human alveolar type II-like A549 cells infected with SeV. The data in FIG. 12 are similar to the data in FIG. 5.

Figure 13:
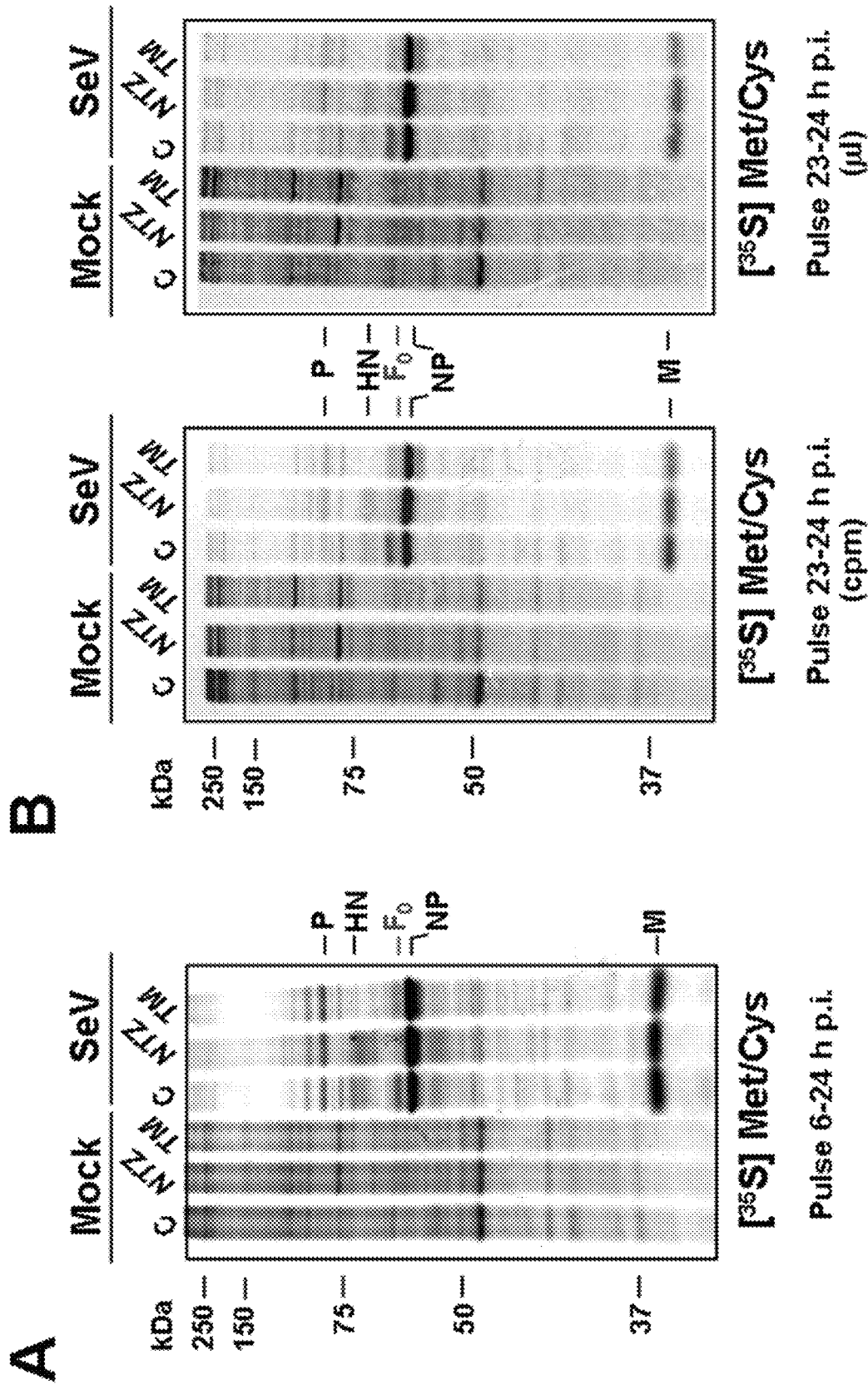

FIG. 13A-B show the effect of Nitazoxanide on SeV protein synthesis.

(A) Autoradiography of [$^{35}$S]Met/Cys-labeled proteins (long-pulse, 18 h started at 6 h p.i.) from mock-infected (Mock) or SeV-infected (SeV) AGMK cells treated with 10 µg/ml NTZ, 2.5 µg/ml tunicamycin (TM) or vehicle (C) after virus adsorption. Viral proteins are indicated. (B) Autoradiography of [$^{35}$S]Met/Cys-labeled proteins (short-pulse, 1 h) at 24 h p.i. from mock-infected or SeV-infected cells treated as in (A). Samples containing equal amounts of radioactivity (right panel, cpm) or equal amounts of proteins (left panel, ml) were processed for SDS-PAGE and autoradiography.

Figure 7:
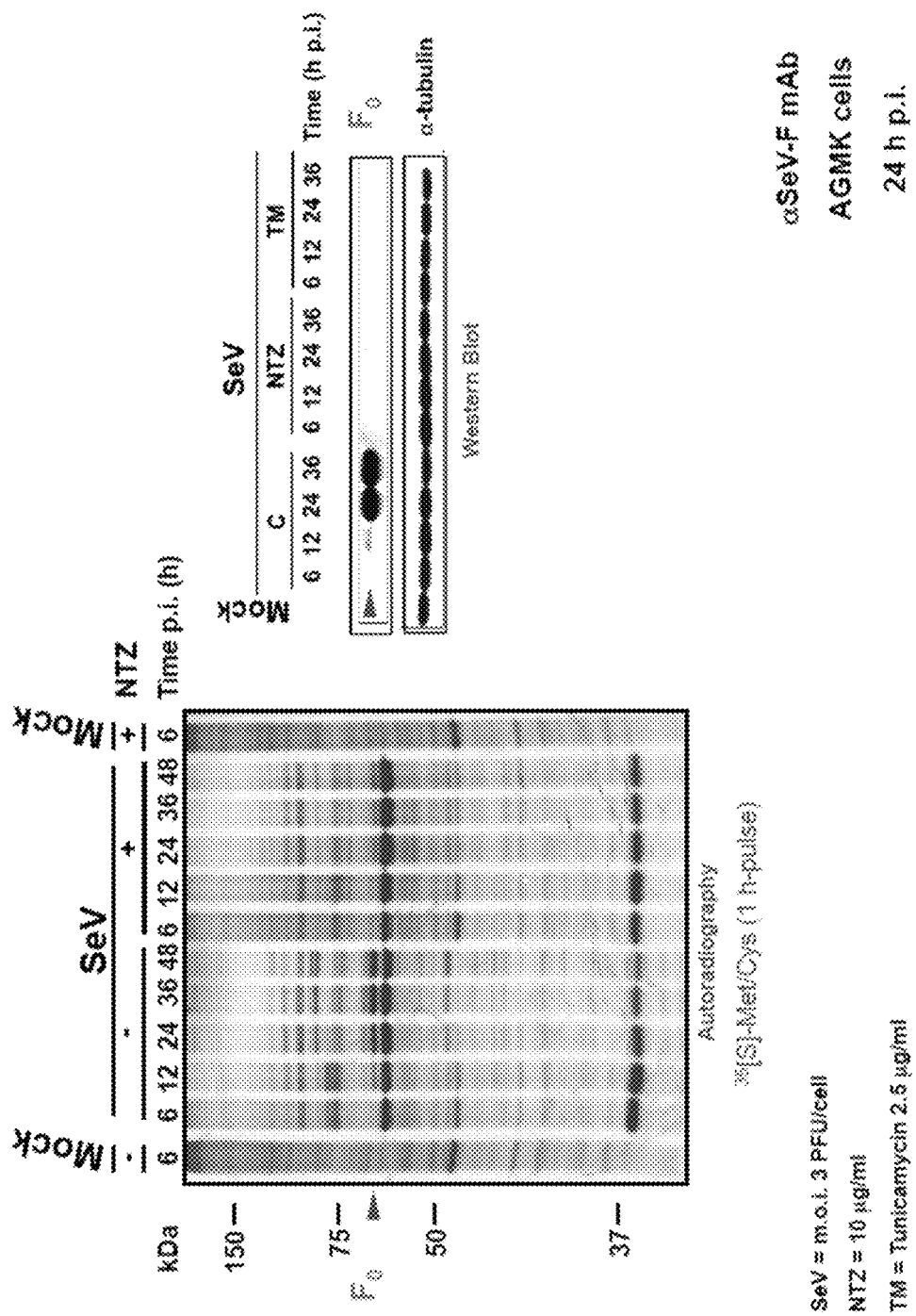
FIG. 7 presents SDS-PAGE and Western Blot data demonstrating effect of Nitazoxanide on SeV-F protein synthesis.
Figure 14:
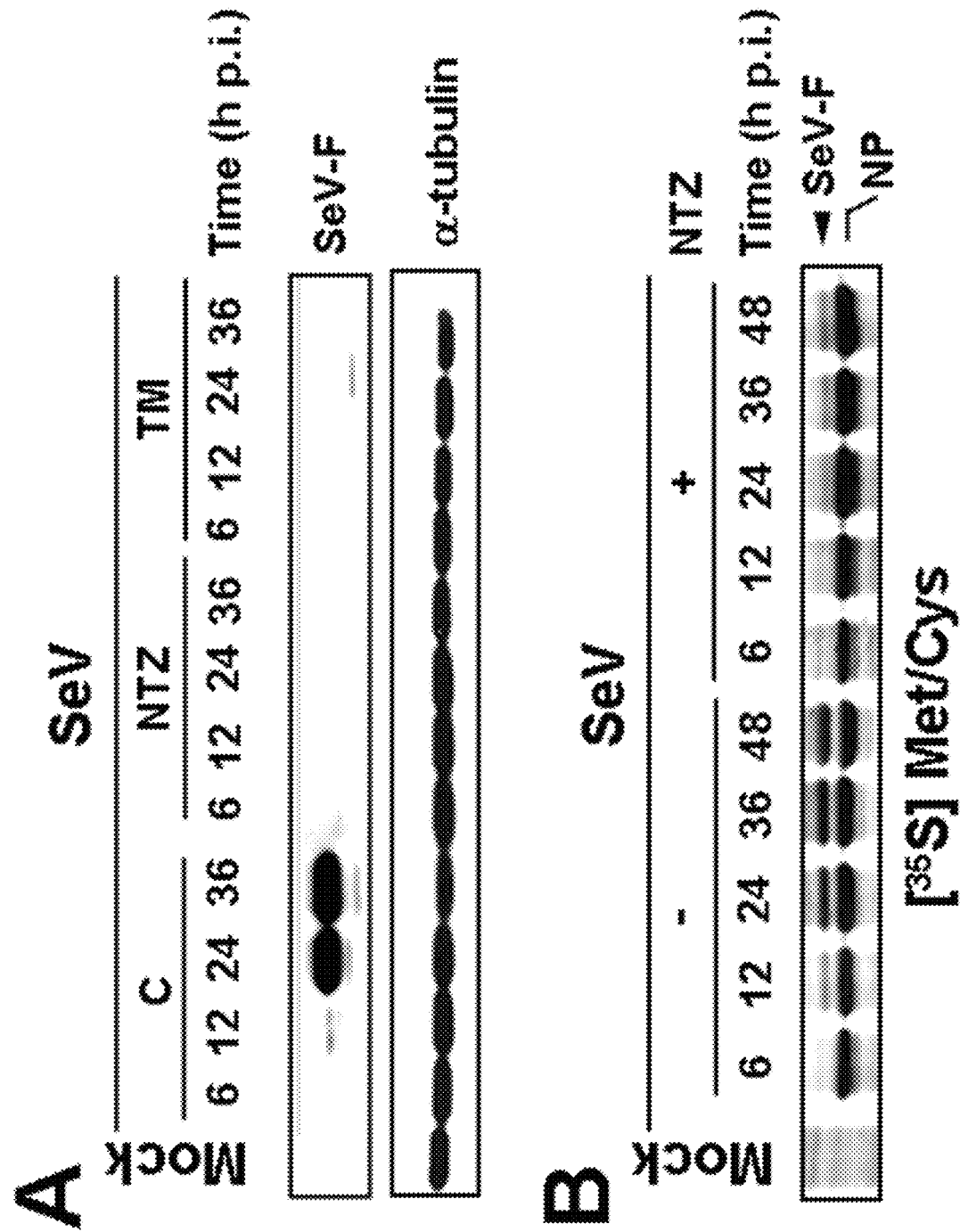

The main SeV proteins were found to be synthesized in large amounts in untreated cells at 24 h p.i. after both long (A, 18 h) and short (B, 1 h) [$^{35}$S]Met/Cys-labeling pulses; no major changes in SeV protein synthesis were detected in NTZ-treated cells, with the exception of the disappearance of a band of approximately 65-70 kDa molecular mass, subsequently identified as the mature isoform of the fusion protein precursor $F_0$ (see FIG. 14). The data in FIG. 13A-B are similar to data in FIG. 7.

FIG. 14A-B show the effect of Nitazoxanide on SeV Fusion protein.

(A) Levels of SeV-F protein were detected by Western blot analysis using a monoclonal SeV-F antibody at different times p.i. in SeV-infected AGMK cells treated with 10 µg/ml NTZ, 2.5 µg/ml tunicamycin (TM) or vehicle (C). Mock-infected (Mock) control is shown. Levels of α-tubulin in the same samples are shown as loading control. (B) Autoradiography of [$^{35}$S]-Met/Cys-labeled proteins (1 h-pulse at different times p.i.) from mock-infected (Mock) or SeV-infected AGMK cells treated with 10 µg/ml NTZ or vehicle (C) after virus adsorption. Viral NP and F proteins are indicated.

Figure 8:
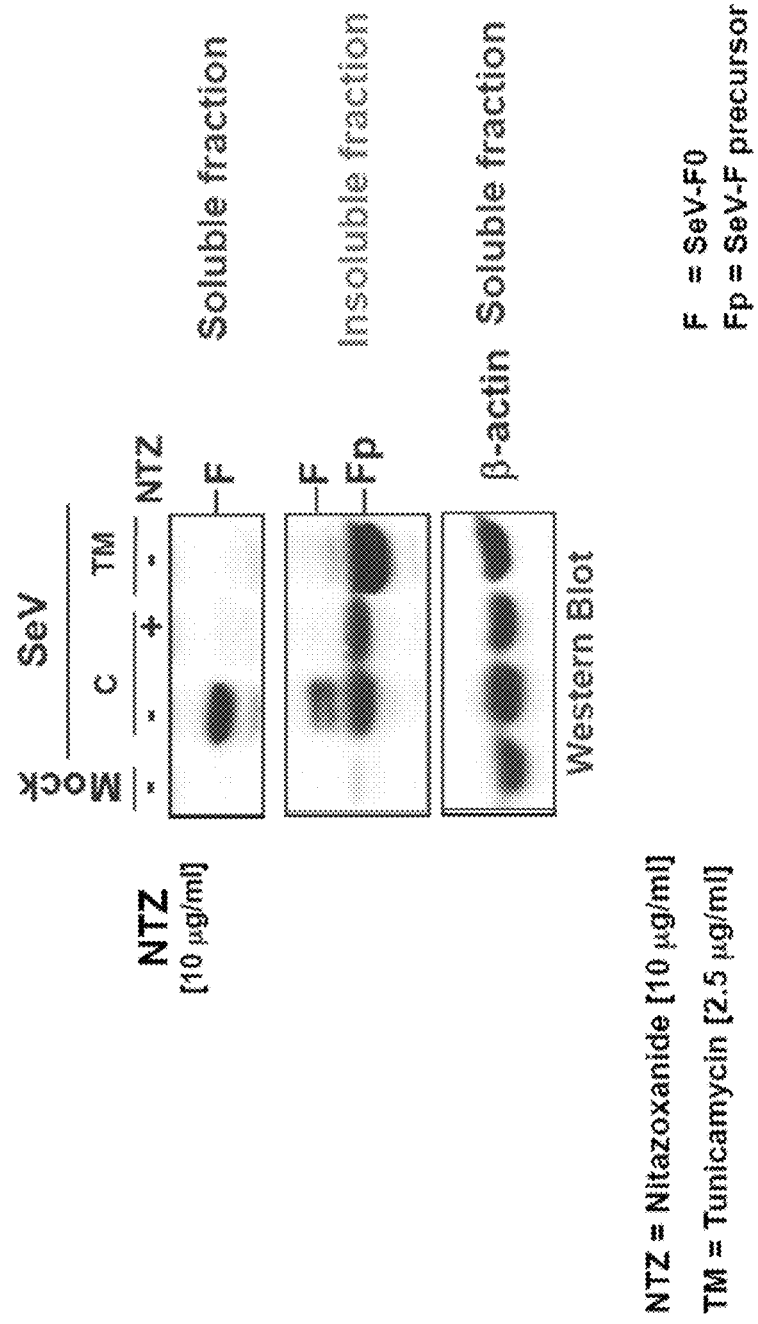
FIG. 8 presents Western Blot data demonstrating detection of the immature form of SeV-F protein in the insoluble fraction of nitazoxanide (NTZ) treated AGMK protein extracts.

The results confirm the absence of the SeV Fusion protein in NTZ-treated cells. Similar results were shown in TM-treated cells. The data in FIG. 14A-B are similar to data in FIG. 8.

Figure 15:
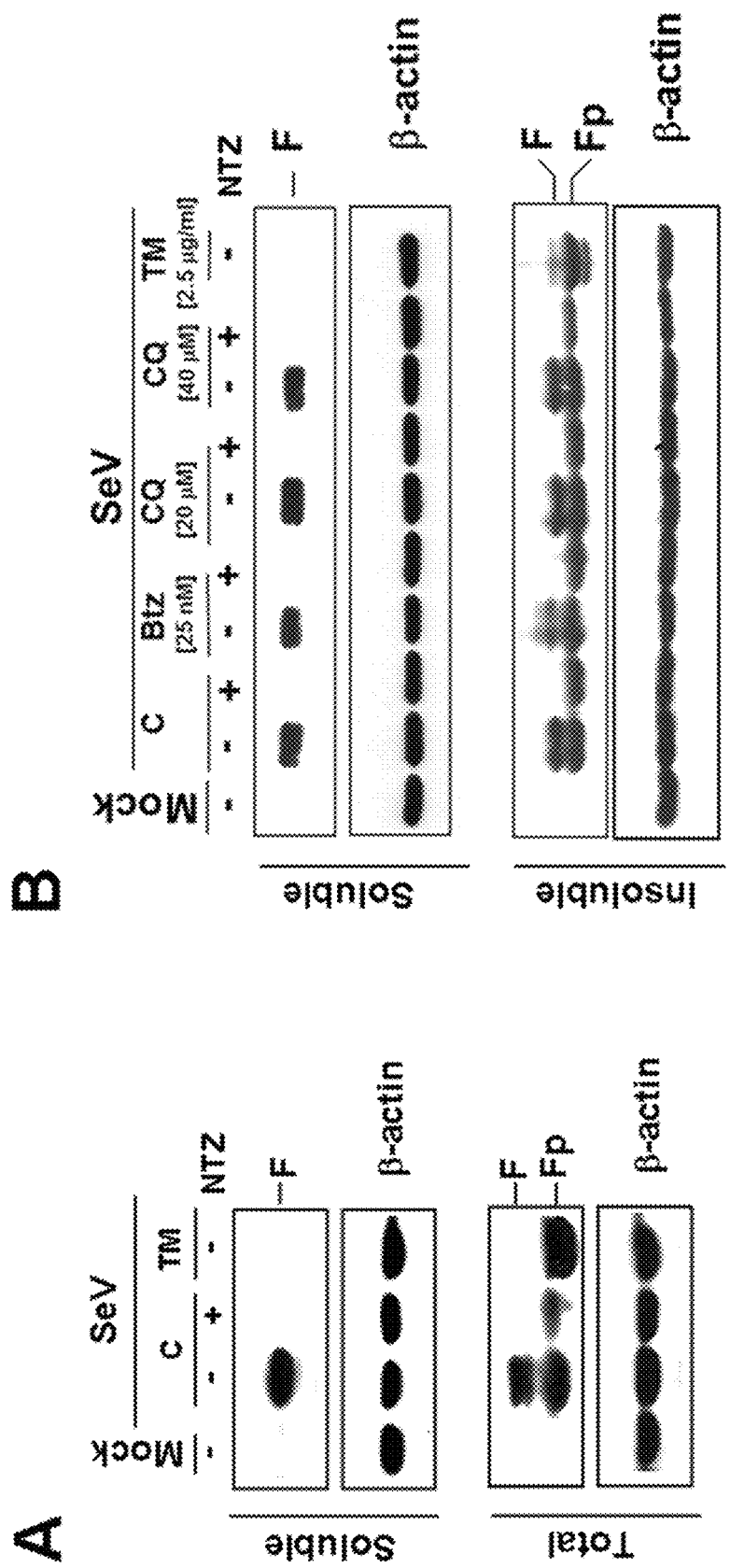

FIG. 15A-B show that nitazoxanide causes SeV-F protein insolubilization.

Western blot analysis for SeV-F and β-actin in mock-infected or SeV-infected AGMK cells treated with 10 µg/ml NTZ, 2.5 µg/ml tunicamycin (TM) or vehicle (C) in the presence (+) or the absence (−) of the proteasome inhibitor bortezomib (Btz, 25 nM), or the autophagy inhibitor chloroquine (CQ, 20 or 40 µM). (A). Soluble fractions of cell lysates extracted with Buffer-B (Soluble) or total cell lysates from parallel samples extracted with Laemmli sample Buffer (Total) are indicated. (B) Immunoblot for SeV-F and β-actin of Soluble and Insoluble fractions of whole-cell extracts extracted with Buffer-B from AGMK cells treated as indicated. Insoluble fractions were processed as described in Materials and Methods. Fp indicates the faster-migrating F form in NTZ-treated cells.

Figure 9:
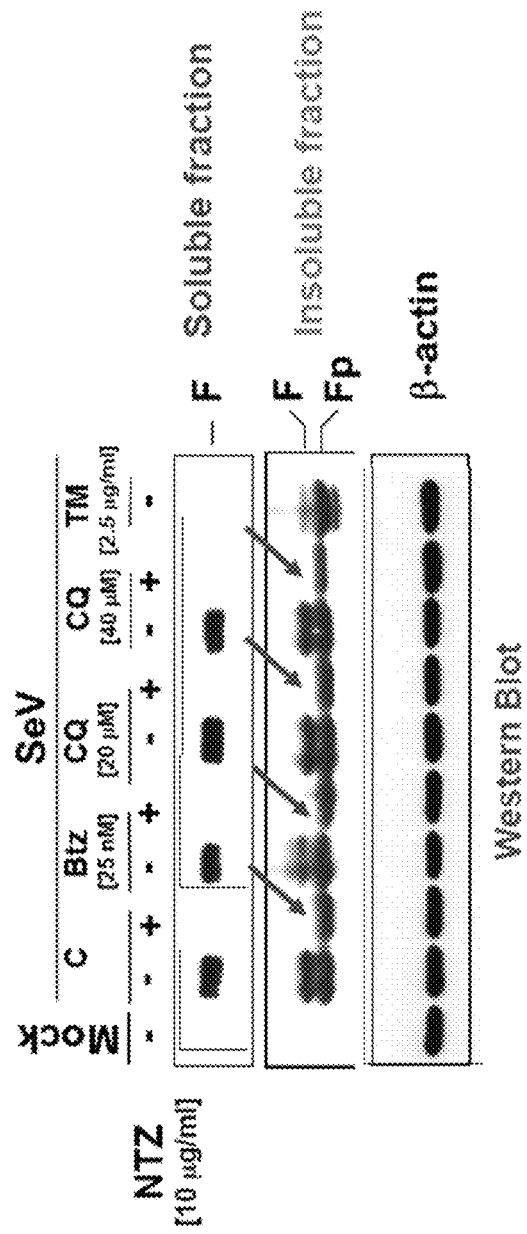
FIG. 9 presents Western Blot data demonstrating detection of the immature form of SeV-F protein in the insoluble fraction of nitazoxanide (NTZ) treated AGMK protein extracts.
Figure 11:
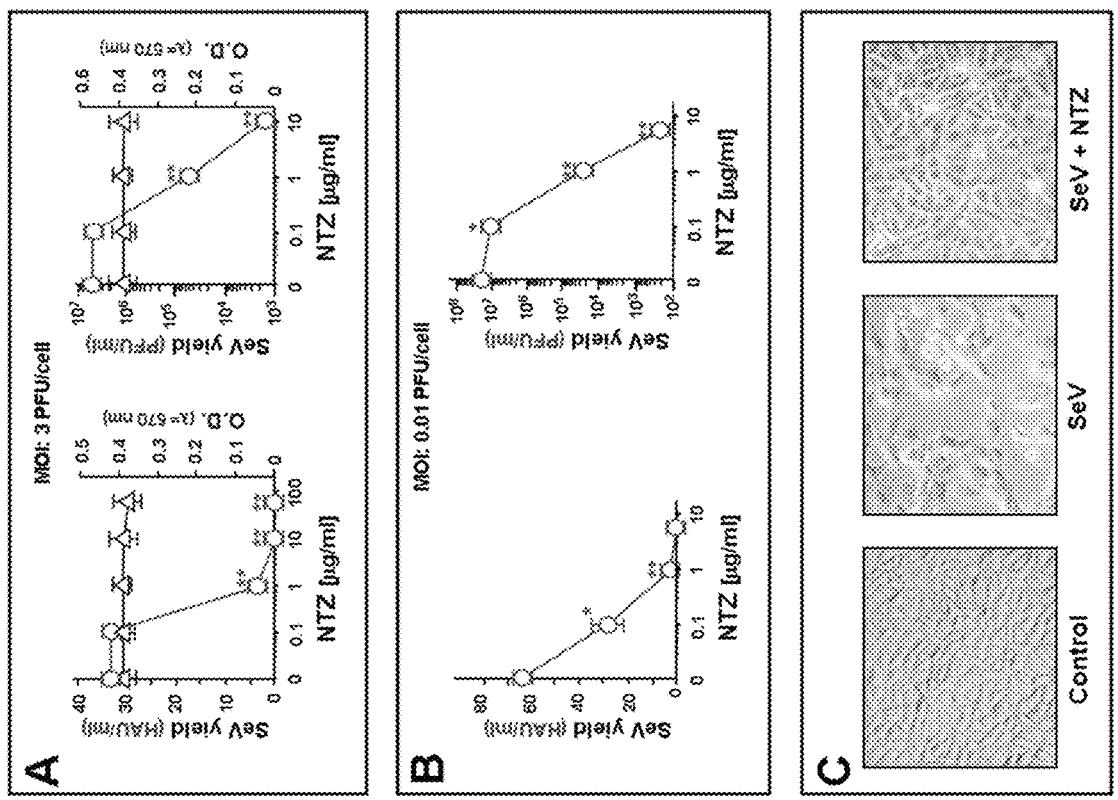
FIG. 11A-C illustrate inhibition of SeV parainfluenza virus by nitazoxanide in AGMK cells. A,B. NTZ inhibits SeV replication under single-step (A) and multistep (B) virus growth conditions. Monkey kidney AGMK cells infected with SeV were treated with different concentrations of NTZ or vehicle immediately after the virus adsorption period. Virus yield (○) was determined at 24 (A) or 48 (B) h post infection (p.i.) by hemagglutinin titration (right panels) and plaque assay (left panels). Virus yield, expressed in HA units (HAU)/ml or PFU/ml, represents the mean±SD of quadruplicate samples. *=p<0.05; **=p<0.01. Cell viability of mock-infected cells (Δ) was determined by MTT assay. (C) Cytoprotective effect of NTZ (10 µg/ml) in SeV-infected AGMK cells at 24 h p.i.

F protein level reduction in NTZ-treated cells was not prevented by the proteasome inhibitor bortezomib or by the autophagy inhibitor chloroquine, indicating an effect independent of proteasome- or autophagy-mediated degradation; instead the F-protein was found in an insoluble state in NTZ-treated cells, indicating that an alteration in protein processing/maturation could lead to the formation of F-protein aggregates present in an insoluble state. The data in FIG. 15A-B are similar to data in FIG. 9.

Figure 16:
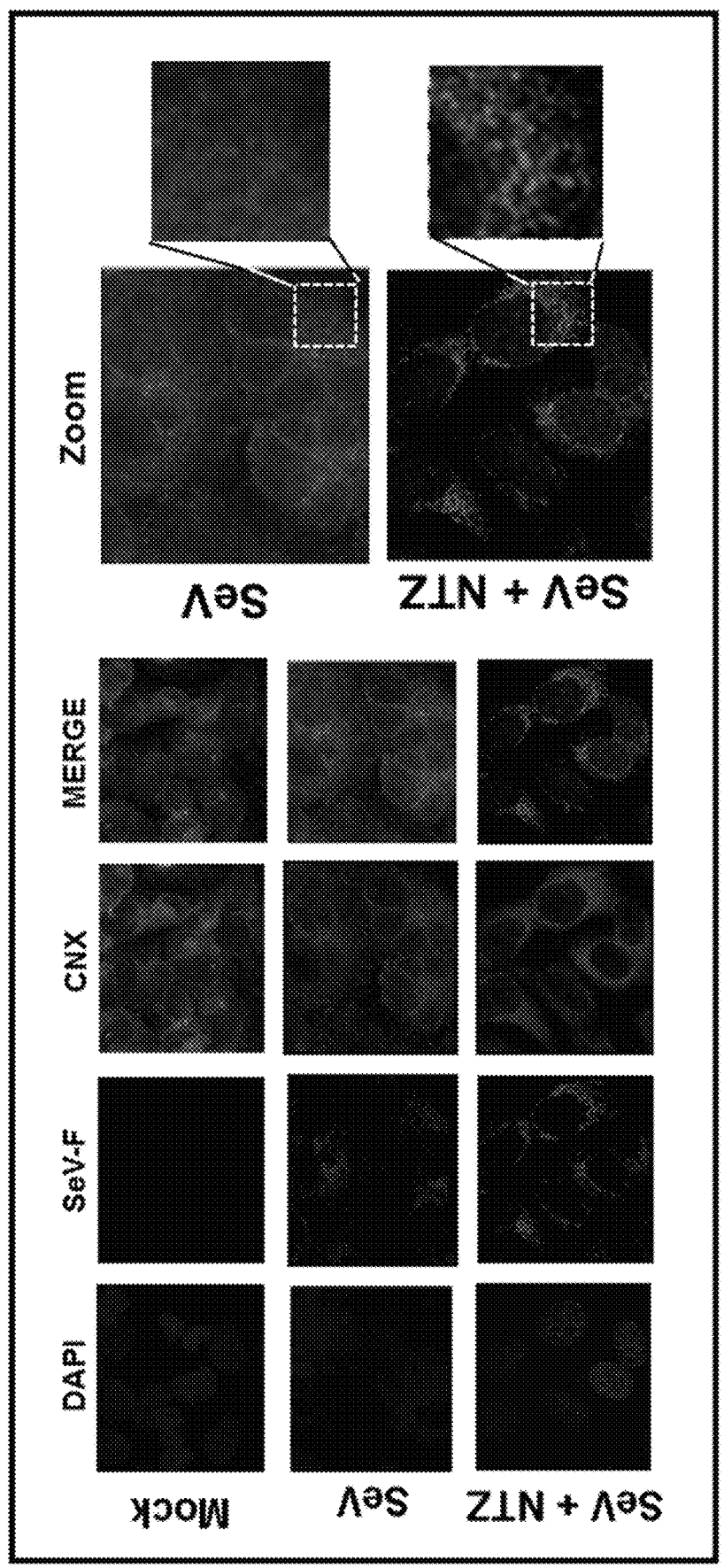

FIG. 16 provides evidence of the presence of large SeV-F protein aggregates in nitazoxanide-treated cells.

Immunoconfocal-microscopy of mock-infected (Mock) and SeV-infected AGMK cells treated with NTZ (10 µg/ml) or vehicle for 24 h, labeled with anti-calnexin (CNX, green) and anti-SeV-F (red) antibodies. Nuclei are stained with DAPI (blue). Images were captured with Olympus Fluoview FV-1000 confocal laser scanning system. The overlay of the three fluorochromes (MERGE) and Zoom images are shown (bar, 7 µm).

Immunoconfocal-microscopy studies confirm the presence of large F-protein aggregates in the ER of NTZ-treated cells.

Figure 17:
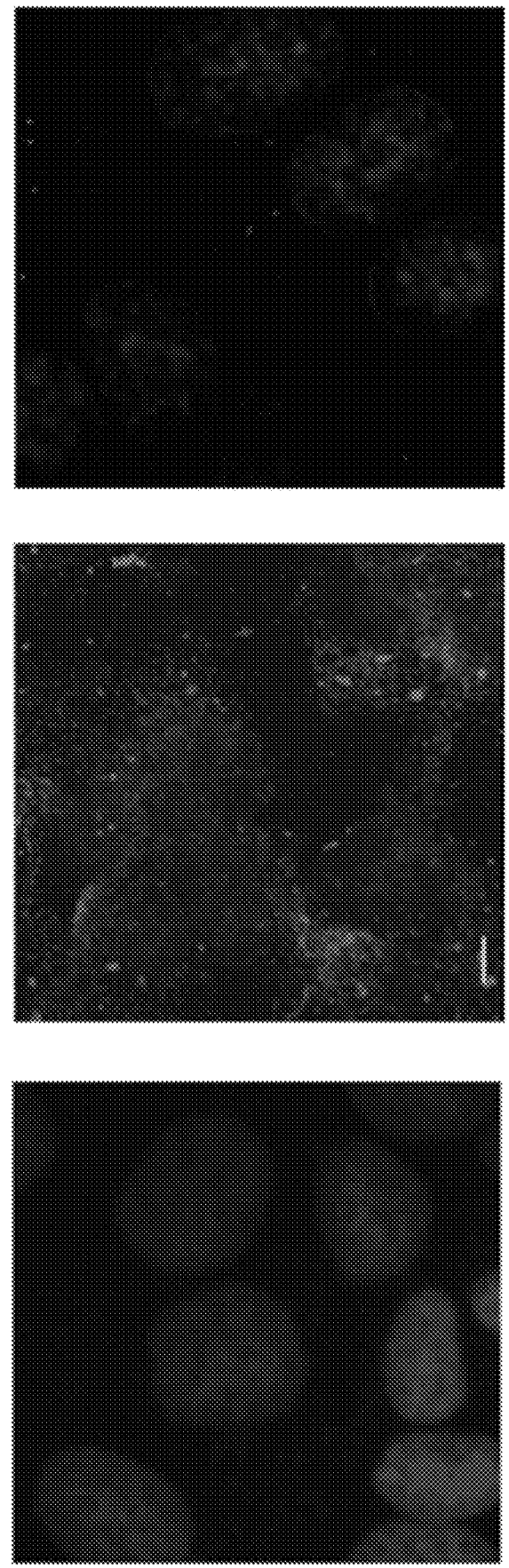

FIG. 17 shows that nitazoxanide inhibits SeV-F glycoprotein transport to the cell surface.

Levels of SeV-F plasma-membrane glycoproteins (red) were detected at 24 h p.i. by confocal immunofluorescence microscopy in SeV-infected AGMK cells treated with 10 µg/ml NTZ or vehicle (SeV). Mock-infected (Mock) cells are shown as control. Nuclei are stained with Hoechst (blue). Images were captured with Olympus Fluoview FV-1000 confocal laser scanning system. The overlay of the two fluorochromes is shown (bar=10 µm).

The presence of the F-protein could not be detected on the host cell surface of NTZ-treated cells, confirming that the alteration in the F protein processing/maturation prevents its transport to the cell membrane.

FIG. 18A-B show that nitazoxanide causes Hendra virus (HeV) and Respiratory Syncytial virus (RSV) F protein insolubilization.

A. Western blot analysis for HeV-F and α-tubulin of HeLa cells mock-transfected or transfected with the HeV-F ORF C-Flag tag construct expressing the HeV-F protein, as described in Materials and Methods, and treated with 5 µg/ml NTZ (C+), 2.5 µg/ml tunicamycin (TM) or vehicle (C−). B. Western blot analysis for RSV-F and α-tubulin of HeLa cells mock-transfected or transfected with the RSV-F ORF C-Flag tag construct expressing the RSV-F protein, as described in Materials and Methods, and treated with 5 µg/ml NTZ (C+), 2.5 µg/ml tunicamycin (TM) or vehicle (C−). A,B. Soluble fractions of cell lysates extracted with Buffer-B (Soluble) or total cell lysates from parallel samples extracted with Laemmli sample Buffer (Total), as described in Materials and Methods, are indicated. HeV-F and RSV-F proteins were detected using anti-FLAG antibodies. Fp indicates the faster-migrating F form in TM-treated cells.

HeV and RSV F-protein was mostly detected in an insoluble state in NTZ-treated cells, indicating that, similarly to the SeV F protein, an alteration in protein processing/maturation could lead to the formation of F-protein aggregates present in an insoluble state.

Figure 19:
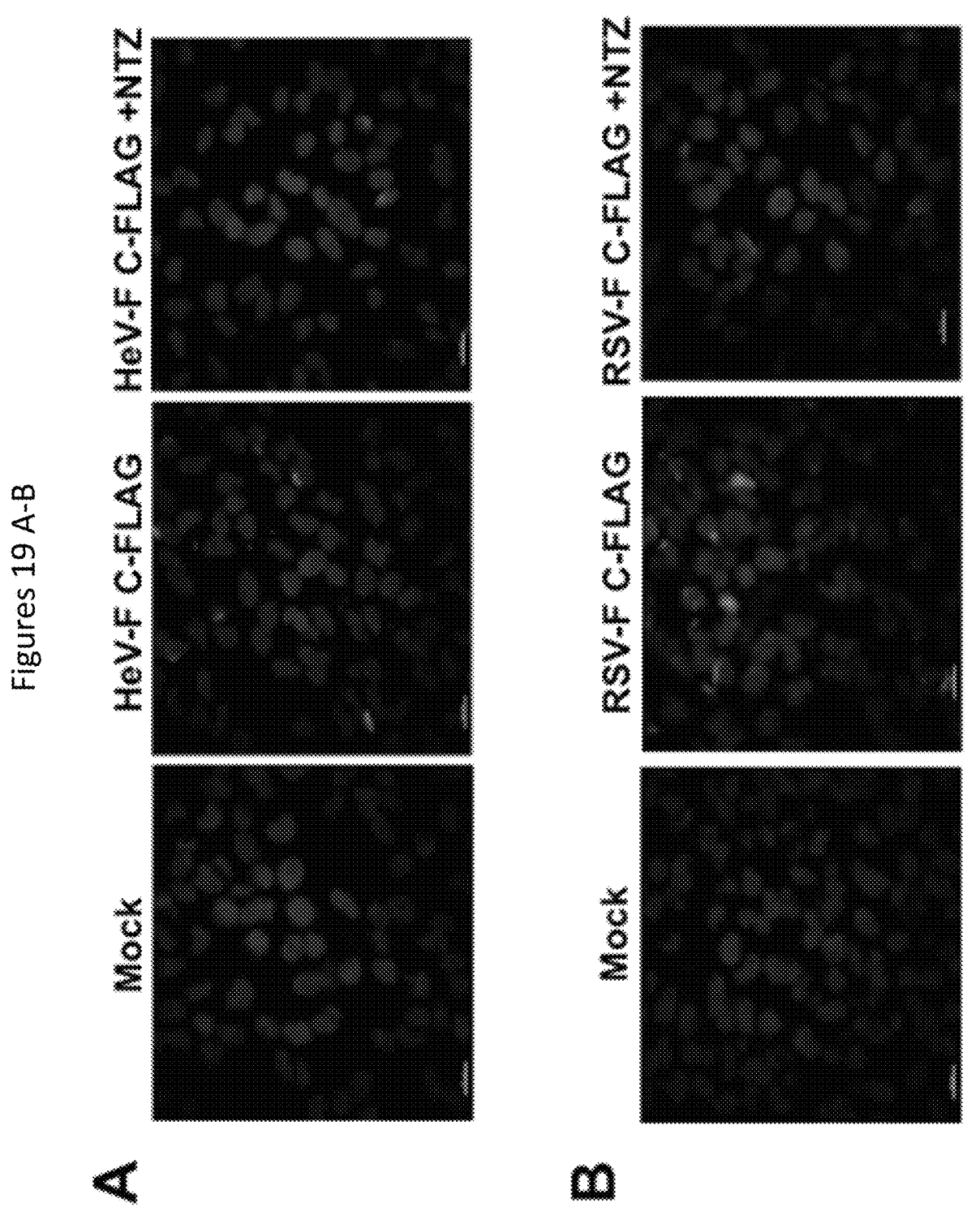

FIG. 19A-B show that nitazoxanide inhibits HeV-F and RSV-F glycoprotein transport to the cell surface.

A. Levels of HeV-F plasma-membrane glycoproteins (red) were detected at 24 h p.i. by confocal immunofluorescence microscopy in non-permeabilized HeLa cells mock-transfected or transfected with the HeV-F ORF C-Flag tag construct expressing the HeV-F protein, as described in Materials and Methods, and treated with 5 µg/ml NTZ or vehicle. B. Levels of RSV-F plasma-membrane glycoproteins (red) were detected at 24 h p.i. by confocal immunofluorescence microscopy in non-permeabilized HeLa cells mock-transfected or transfected with the RSV-F ORF C-Flag tag construct expressing the RSV-F protein, as described in Materials and Methods, and treated with 5 µg/ml NTZ or vehicle. A,B. F proteins were detected using anti-FLAG antibodies (red). Nuclei are stained with Hoechst (blue). Mock-transfected (Mock) cells are shown as control. Images were captured with Olympus Fluoview FV-1000 confocal laser scanning system. The overlay of the two fluorochromes is shown.

The presence of the F-protein was detected at a lower level on the host cell surface of NTZ-treated cells indicating that, similarly to the SeV F protein, the alteration in the HeV and RSV F protein processing/maturation prevents its transport to the cell membrane.

In the case of RSV infection, nitazoxanide was found to possess antiviral activity against RSV-A2 in HeLa cells at non cytotoxic doses, with an $IC_{50}$ of 0.3 µg/ml and an $IC_{90}$ of 0.8 µg/ml (for details of RSV infection see Materials and Methods). The data in FIG. 19A-B are similar to data in FIG. 10.

RELATED DOCUMENTS

The following documents, which are all incorporated by reference, may be useful for understanding the present disclosure: U.S. Pat. Nos. 9,351,937; 9,126,992; 9,107,913; 9,023,877; 8,895,752; 8,846,727; 8,772,502; 8,633,230; 8,524,278; 8,124,632; 7,645,783; 7,550,493; 7,285,567; 6,117,894; 6,020,353; 5,968,961; 5,965,590; 5,935,591; 5,886,013; 5,859,038; 5,856,348; 5,387,598; U.S. patent application publications nos. 2015-025768; 2014-0065215; 2012-0294831; 2016-0243087; PCT publication no. WO2016077420; J. Biol. Chem., 2009 Oct. 23; 284(43): 29798-29808; Antiviral Research, 110(2014): 94-103; Biochim Biophys Acta., 2003 Jul. 11; 1614(1):73-84.

Definition of Terms

Unless otherwise specified, "a" or "an" means "one or more."

As used herein, the term "viral infection" describes a diseased state, in which a virus invades a healthy cell, uses the cell's reproductive machinery to multiply or replicate and ultimately lyse the cell resulting in cell death, release of viral particles and the infection of other cells by the newly produced progeny viruses. Latent infection by certain viruses is also a possible result of viral infection. An acute virus infection is usually characterized by a rapid onset of a disease, a relatively brief period of symptoms, and resolution within days to a few weeks. It is usually accompanied by early production of infectious virions and elimination of infection by the host immune system. Acute viral infections are responsible for epidemics of disease involving millions of individuals each year. When vaccines are not available or not used, acute infections can be difficult to control since an infected individual is usually infectious prior to becoming ill. This makes it exceedingly difficult to control acute infections in large populations and densely populated areas such as colleges, nursing homes, military bases or ships. Children, the elderly and immunocompromised individuals are more susceptible to complications from these normally self-limiting infections.

The term "a disease or condition caused by or associated with a virus" may refer to a viral infection caused by the virus and/or one or more of its symptoms, which may be associated with the viral infection.

As used herein, the term "treating and/or preventing a disease or condition caused by or associated with a virus" may include at least one of the following: inhibiting the replication of the virus, inhibiting viral transmission, preventing the virus from establishing itself in its host, ameliorating or alleviating the symptoms or progression of the disease caused by the virus. The treatment is considered therapeutic if there is at least one of a reduction in viral load, decrease in mortality and/or morbidity related with the disease, decrease in the progression of the disease or a shorter duration of the disease. In certain embodiments, "treating and/or preventing a disease or condition caused by or associated with a virus" may include increased survival among subjects affected with the disease or condition caused by or associated with influenza virus and treated with an active agent, such as a thiazolide compound, compared to subjects affected with the disease or condition but not treated with the active agent. In certain embodiments, "treating and/or preventing a disease or condition caused by or associated with a virus" may include reduction of a viral load in a subject affected with the disease or condition caused by or associated with the virus upon administering an active agent. Yet in some embodiments, "treating and/or preventing a disease or condition caused by or associated with a virus" may include ameliorating or alleviating the symptoms or progression of the disease caused by the virus.

Disclosure

The present inventors discovered that certain thiazolide compounds may be effective against viruses belonging to the Picornaviridae and Paramyxoviridae viral families.

In particular, such compounds may be useful for treating or preventing a disease or condition caused by or associated with a virus belonging to the Picornaviridae and Paramyxoviridae viral families.

Picornaviridae Viral Family

The Picornaviridae family is a (+)ssRNA viral family. Vertebrates, including humans, may serve as natural hosts for *picornaviruses*. There are currently 50 species in this family, divided among 29 genera. The genera of the Picornaviridae family include: *Aphthovirus* genus, which includes Bovine rhinitis A virus, Bovine rhinitis B virus, Equine rhinitis A virus, Foot-and-mouth disease virus; *Aquamavirus* genus, which includes Aquamavirus A; *Avihepatovirus* genus, which includes Duck hepatitis A virus; *Cardiovirus* genus, which includes Encephalomyocarditis virus, *thilovirus, Cosavirus; Dicipivirus* genus, which includes *cadicivirus* A; *Enterovirus* genus, which includes *enteroviruses* A-J and rhinoviruses A-C; *Erbovirus* genus, which includes Equine rhinitis B virus; *Hepatovirus* genus, which includes Hepatitis A virus; *Kobuvirus* genus, which includes Aichivirus A, Aichivirus B and Aichivirus C; *Megrivirus* genus, which includes Melegrivirus A, Human *parechovirus*; Ljungan virus; *Piscevirus* genus, which includes Fathead minnow *picornavirus; Salivirus* genus, which includes Salivirus A; *Sapelovirus* genus, which includes porcine *sapelovirus*, simian *sapelovirus* and avian *sapelovirus; Senecavirus* genus, which includes Seneca Valley virus; *Teschovirus* genus, which includes Porcine *teschovirus; Tremovirus* genus, which includes avian encephalomyelitis virus. Diseases associated with the Picornaviridae family include: paralysis (non-polio and polio-type), summer cold, meningitis, diarrhea caused by *Enteroviruses*; foot-and-mouth disease (*bovine*) caused by *Aphthoviruses*; myocarditis caused by *Cardioviruses*; common cold caused by *Rhinoviruses*; and hepatitis caused by *Hepatoviruses*. Diseases associated with the Picornaviridae family include: paralysis (non-polio and polio-type), summer cold, meningitis, diarrhea caused by *Enteroviruses*; foot-and-mouth disease (*bovine*) caused by *Aphthoviruses*; myocarditis caused by *Cardioviruses*; common cold caused by *Rhinoviruses*; and hepatitis caused by *Hepatoviruses*.

Enterovirus Genus

The Enterovirus genus includes the following twelve species: *Enterovirus* A, *Enterovirus* B, *Enterovirus* C, *Enterovirus* D, *Enterovirus* E, *Enterovirus* F, *Enterovirus* G, *Enterovirus* H, *Enterovirus* J, *Rhinovirus* A, *Rhinovirus* B, *Rhinovirus* C. Within these twelve species are the serotypes: 1) *Coxsackievirus*: a) serotypes CV-A2, CV-A3, CV-A4, CV-A5, CV-A6, CV-A7, CV-A8, CV-A10, CV-A12, CV-A14 & CV-A16 found under the species *Enterovirus* A; b) serotypes CV-B1, CV-B2, CV-B3, CV-B4, CV-B5, CV-B6 & CV-A9 found under the species; *Enterovirus* B; c) serotypes CV-A1, CV-A11, CV-A13, CV-A17, CV-A19, CV-A20, CV-A21, CV-A22 & CV-A24 found under the species *Enterovirus C;* 2) *Echovirus* serotypes E-1, E-2, E-3, E-4, E-5, E-6, E-7, E-9, E-11, E-12, E-13, E-14, E-15, E-16, E-17, E-18, E-19, E-20, E-21, E-24, E-25, E-26, E-27, E-29, E-30, E-31, E-32, & E-33 found under the species *Enterovirus B;* 3) *Enterovirus* a) types EV-A71, EV-A76, EV-A89, EV-A90, EV-A91, EV-A92, EV-A114, EV-A119, SV19, SV43, SV46 & BA13 found under the species Enterovirus A; b) types EV-B69, EV-B73, EV-B74, EV-B75, EV-B77, EV-B78, EV-B79, EV-B80, EV-B81, EV-B82, EV-B83, EV-B84, EV-B85, EV-B86, EV-B87, EV-B88, EV-B93, EV-B97, EV-B98, EV-B100, EV-B101, EV-B106, EV-B107, EV-B110 & SA5 found under the species *Enterovirus* B; c) types EV-C95, EV-C96, EV-C99, EV-C102, EV-C104, EV-C105, EV-C109, EV-C116, EV-C117 & EV-C118 found under the species *Enterovirus* C; d) types EV-D68, EV-D70, EV-D94, EV-D111 & EV-D120 found under the species *Enterovirus* D; e) types: EV-H1 found under the species *Enterovirus* H; f) types: SV6, EV-J103, EV-J108, EV-J112, EV-J115 and EV-J121 found under the species *Enterovirus* J; 4) Human *rhinovirus* a) types HRV-A1, HRV-A2, HRV-A7, HRV-A8, HRV-A9, HRV-A10, HRV-A11, HRV-A12, HRV-A13, HRV-A15, HRV-A16, HRV-A18, HRV-A19, HRV-A20, HRV-A21, HRV-A22, HRV-A23, HRV-A24, HRV-A25, HRV-A28, HRV-A29, HRV-A30, HRV-A31, HRV-A32, HRV-A33, HRV-A34, HRV-A36, HRV-A38, HRV-A39, HRV-A40, HRV-A41, HRV-A43, HRV-A44, HRV-A45, HRV-A46, HRV-A47, HRV-A49, HRV-A50, HRV-A51, HRV-A53, HRV-A54, HRV-A55, HRV-A56, HRV-A57, HRV-A58, HRV-A59, HRV-A60, HRV-A61, HRV-A62, HRV-A63, HRV-A64, HRV-A65, HRV-A66, HRV-A67, HRV-A68, HRV-A71, HRV-A73, HRV-A74, HRV-A75, HRV-A76, HRV-A77, HRV-A78, HRV-A80, HRV-A81, HRV-A82, HRV-A85, HRV-A88, HRV-A89, HRV-A90, HRV-A94, HRV-A95, HRV-A96, HRV-A98, HRV-A100, HRV-A101, HRV-A102 & HRV-A103 found under the species Rhinovirus A; b) types HRV-B3, HRV-B4, HRV-B5, HRV-B6, HRV-B14, HRV-B17, HRV-B26, HRV-B27, HRV-B35, HRV-B37, HRV-B42, HRV-B48, HRV-B52, HRV-B69, HRV-B70, HRV-B72, HRV-B79, HRV-B83, HRV-B84, HRV-B86, HRV-B91, HRV-B92, HRV-B93, HRV-B97, & HRV-B99 found under the species *Rhinovirus* B; c) types HRV-C1, HRV-C2, HRV-C3, HRV-C4, HRV-05, HRV-C6, HRV-C7, HRV-C8, HRV-C9, HRV-C10, HRV-C11, HRV-C12, HRV-C13, HRV-C14, HRV-C15, HRV-C16, HRV-C17, HRV-C18, HRV-C19, HRV-C20, HRV-C21, HRV-C22, HRV-C23, HRV-C24, HRV-C25, HRV-C26, HRV-C27, HRV-C28, HRV-C29, HRV-C30, HRV-C31, HRV-C32, HRV-C33, HRV-C34, HRV-C35, HRV-C36, HRV-C37, HRV-C38, HRV-C39, HRV-C40, HRV-C41, HRV-C42, HRV-C43, HRV-C44, HRV-C45, HRV-C46, HRV-C47, HRV-C48, HRV-C49, HRV-050 & HRV-051 found under the species *Rhinovirus* C; 5) *Poliovirus* serotypes PV-1, PV-2, & PV-3 found under the species *Enterovirus* C.

Coxsackie A viruses are mainly associated with human hand, foot and mouth disease. Coxsackie B viruses can cause signs and symptoms, similar to a "cold," but these viruses also can lead to more serious diseases, including myocarditis (inflammation of the heart); pericarditis (inflammation of the sac lining the heart); meningitis (inflammation of the membranes that line the brain and spinal cord); and pancreatitis (inflammation of the pancreas). *Echoviruses* are a cause of many of the nonspecific viral infections. It is mainly found in the intestine, and can cause nervous disorders. The usual symptoms of Coxsackie and *echovirus* are fever, mild rash, and mild upper respiratory tract (URT) illness.

Diseases caused by viruses belonging to the Enterovirus genus include, but not limited to, poliomyelitis; poly-like syndrome; nonspecific febrile illness, which may have one or more of the following symptoms: fever, muscle pain, sore throat, gastrointestinal distress/abdominal discomfort, and headache; septic meningitis; Bornholm disease or epidemic pleurodynia, which may be characterized by one or more of the following symptoms: severe paroxysmal pain in the chest and abdomen, fever, nausea, headache, and emesis; pericarditis and/or myocarditis, which may have one or more of the following symptoms: fever, dyspnea and chest pain; acute hemorrhagic conjunctivitis; herpangina, which may involve one or more of the following symptoms: vesicular rash in the oral cavity and on the pharynx, high fever, sore throat, malaise, dysphagia, loss of appetite, back pain, and headache; hand, foot and mouth disease.

Paramyxoviridae Viral Family

The Paramyxoviridae family is a (−)ssRNA viral family. Humans, vertebrates, and birds serve as natural hosts for *paramyxoviruses*. There are currently 36 species in this family, divided among 18 genera. Diseases associated with the Paramyxoviridae family include: measles, mumps, respiratory tract infections. Paramyxoviridae is split into two sub-families, Paramyxovirinae and Pneumovirinae. The genera of the Paramyxoviridae family include: *Aquaparamyxovirus* genus, which includes Atlantic salmon *paramyxovirus; Avulavirus* genus, which includes Avian *paramyxoviruses* 1-12, Goose *paramyxovirus* and Newcastle disease virus; *Ferlavirus* genus, which includes Fer-de-Lance *paramyxovirus; Henipavirus* genus, which includes Hendra virus, Nipah virus and Cedar virus; *Morbillivirus* genus, which includes canine distemper virus, catecean morbillius virus, measles virus, peste-des-petits-ruminants virus, phocine distemper virus, rinderpest virus; *Respirovirus* genus, which includes Sendai virus, human parainfluenza virus type 1 and human parainfluenza virus type 3; *Rubulavirus* genus, which includes mumps virus, human parainfluenza virus type 2 and human parainfluenza virus type 4; Tupaia *paramyxovirus* (TPMV)-like viruses; *Metapneumovirus* genus, which includes avian *metapneumovirus* and human *metapneumovirus; pneumovirus* genus, which includes human respiratory syncytial virus (HRSV), bovine respiratory syncytial virus, ovine respiratory syncytial virus, caprine respiratory syncytial virus, pneumonia virus of mice. *Henipaviruses*, such as Hendra virus, Nipah virus and Cedar virus can cause an illness or even death in domestic animals, including equines, felines, pigs, as well as in humans.

The Paramyxoviridae family includes Human parainfluenza viruses (HPIV) types 1-4. HPIV-1 may be a cause of croup, also known as laryngotracheobronchitis, which is a type of respiratory infection. The infection may lead to swelling inside the trachea, which interferes with normal breathing and produces the classic symptoms of "barking" cough, stridor, and a hoarse voice. Fever and runny nose may also be present. HPIV-2 may also be a cause of croup as a cause of other upper and lower respiratory tract illnesses. HPIV-3 may be a cause of with bronchiolitis and pneumonia. HPIV-3 may principally target young children, such as those aged <1 year. Bronchiolitis is inflammation of the bronchioles, the smallest air passages of the lungs. It presents with coughing, wheezing and/or shortness of breath which can cause some children difficulty in feeding. Pneumonia is an inflammatory condition of the lung affecting primarily the microscopic air sacs known as alveoli. Typical signs and symptoms include a varying severity and combination of productive or dry cough, chest pain, fever, and trouble breathing, depending on the underlying cause.

Sendai virus (SeV), also known as murine parainfluenza virus type 1 or hemagglutinating virus of Japan (HVJ) is responsible for a highly transmissible respiratory tract infection in mice, hamsters, guinea pigs, rats, and occasionally pigs. Symptoms of the Sendai virus caused infection include sneezing, hunched posture, respiratory distress, porphyrin discharge form eyes and/or nose, lethargy, failure to thrive in surviving babies and young rats, anorexia.

Viruses belonging to the genus *Pneumovirus*, such as human respiratory syncytial virus, may cause a number of diseases involved with respiratory illness, which may range from a less-severe upper-respiratory illness to severe bronchiolitis or pneumonia. Symptoms of such diseases may include mild symptoms such as rhinitis, coughing, and decreased appetite and more serious symptoms, such as wheezing, difficulty breathing, fever, bronchiolitis and pneumonia.

In some embodiments, a thiazolide compound, such as nitazoxanide and/or tizoxanide, may reduce a duration of symptoms caused by or associated with human respiratory syncytial virus. For example, a thiazolide compound, such as nitazoxanide and/or tizoxanide, may reduce a duration of symptoms caused by or associated with human respiratory syncytial virus by at least 12 hours or at least 24 hours or at least 36 hours or at least 48 hours or at least 60 hours or at least 72 hours or at least 84 hours or at least 96 hours or at least 108 hours or at least 120 hours or at least 132 hours or at least 144 hours. For examples, in some embodiments, a duration of symptoms caused by or associated with human respiratory syncytial virus may be reduced by from 12 hours to 144 hours or from 24 hours to 132 hours or from 36 hours to 120 hours or from 48 hours to 108 hours or from 60 hours to 96 hours or from 66 hours to 90 hours from 72 hours to 84 hours or any subrange or value within these ranges.

In some embodiments, the thiazolide compound may be nitazoxanide (1, see formula below) or a pharmaceutically acceptable salt thereof. Nitazoxanide is a licensed product in the United States for the treatment of infectious gastroenteritis. In some embodiments, the thiazolide compound may be tizoxanide or its pharmaceutically acceptable salt, also shown below.

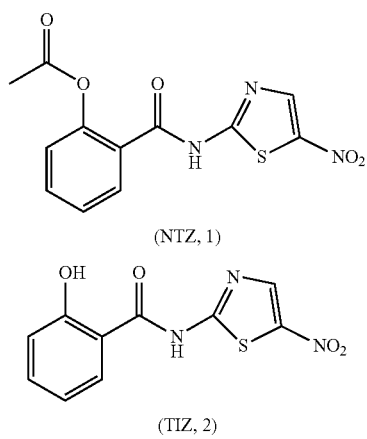

(NTZ, 1)

(TIZ, 2)

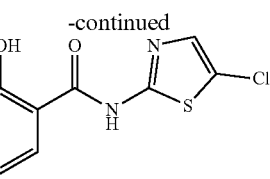

RM-4848

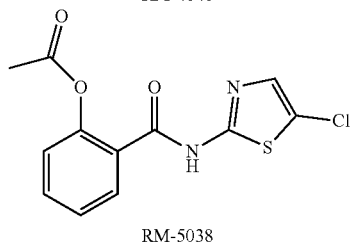

RM-5038

In some embodiments, nitazoxanide and tizoxanide may be used together as a combination.

In some embodiments, the thiazolide compound may be RM-4848, which is a substituted thiazolide having the same structure as tizoxanide, but including a chloro group substituted for the nitro group, thus resulting in the compound N-(5-chlorothiazol-2-yl)-2-hydroxybenzamide. In some embodiments, the thiazolide compound may be RM-5038, which is an ester prodrug of RM-4848. RM-4848 and RM-5038 are disclosed for example, in U.S. patent application publication no. 20120294831.

Thiazolide compounds may be synthesized, for example, according to published procedures U.S. Pat. Nos. 3,950,351 and 6,020,353, PCT WO2006042195A1 and US2009/0036467A. Other suitable thiazolide compounds are disclosed in U.S. Pat. Nos. 7,645,783, 7,550,493, 7,285,567, 6,117,894, 6,020,353, 5,968,961, 5,965,590, 5,935,591, and 5,886,013.

In some embodiments, when used against a virus belonging to the Paramyxoviridae family, the thiazolide compound, such as nitazoxanide and/or tizoxanide, or RM-4848 and its ester (such as RM5038), may reduce an intracellular level of the mature F-protein of the virus. For example, when used against a virus belonging to the *Respirovirus* genus, such as Sendai virus, the thiazolide compound may reduce an intracellular level of such viral protein. When used against a virus belonging to the *Pneumovirus* genus, such as respiratory syncytial virus, the thiazolide compound may reduce an intracellular level of such viral protein. When used against a virus belonging to the *Henipavirus* genus, such as Hendra virus, the thiazolide compound may reduce an intracellular level of such viral protein.

In some embodiments, when used against a virus belonging to the Picornaviridae family, such as a virus belonging to the *Enterovirus* genus, the thiazolide compound, such as nitazoxanide and/or tizoxanide, may be administered together with a direct-acting antiviral agent that inhibits replication of viruses belonging to the Picornaviridae family.

Direct-acting antiviral agents include, but are not limited to, 3C protease inhibitors, such as rupintrivir, Pyrazoles 17 and 18, and nucleoside analog inhibitors, such as MK-0608. Preferably, a direct-acting antiviral agent is administered in an effective amount, which is an amount necessary to achieve a desired effect when the direct-acting antiviral agent is used together with a thiazolide compound, such as nitazoxanide and/or tizoxanide.

A thiazolide compound, such as nitazoxanide and/tizoxanide, may be administered concurrently or subsequently with a neuraminidase inhibitor.

When a virus belongs to the *Enterovirus* genus, administering of a thiazolide compound, such as nitazoxanide and/or tizoxanide, alone or together with a direct-acting antiviral agent may alleviate at least one symptom of a disease or condition caused by or associated with such virus, which symptom may be, for example, fever, cough, sore throat, nasal obstruction, fatigue, headache, myalgia, and/or feverishness. For example, in some embodiments, when a virus belongs to the *Enterovirus* genus, administering of a thiazolide compound, such as nitazoxanide and/or tizoxanide, alone or together with a direct-acting antiviral agent may a) reduce fever caused by or associated with a disease or condition caused by or associated with such virus and b) alleviate at least one symptom of the disease or condition, which symptom may be, for example, cough, sore throat, nasal obstruction, fatigue, headache, myalgia, and/or feverishness.

In some embodiments, wherein administering of a thiazolide compound, such as nitazoxanide and/or tizoxanide, alone or together with a neuraminidase inhibitor, such as oseltamivir, may a) reduce the fever caused by or associated with the disease or condition, and b) alleviate at least one respiratory symptom caused by or associated with the disease or condition and at least one constitutional symptom associated with the disease or condition, wherein the at least one respiratory symptom is selected from cough, sore throat, and/or nasal obstruction and wherein the at least constitutional symptom is selected from fatigue, headache, myalgia, and feverishness.

The term "salt" may be used in its broadest sense. For example, the term "salt" includes hydrogen salts and hydroxide salts with ions of the present compound. In some embodiments, the term salt may be a subclass referred to as pharmaceutically acceptable salts, which are salts of the present compounds having a pharmacological activity and which are neither biologically nor otherwise undesirable. In all embodiments, the salts can be formed with acids, such as, without limitation, hydrogen, halides, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycero-phosphate, hemisulfate, heptanoate, hexanoate, hydrochloride hydrobromide, hydroiodide, 2-hydroxyethane sulfonate, lactate, maleate, methanesulfonate, 2-naphthalenesulfonate, nicotinate, oxalate, thiocyanate, tosylate, and undecanoate. In all embodiments, the salts can be formed with bases, such as, without limitation, hydroxide, ammonium salts, alkali metal salts such as lithium, sodium and potassium salts, alkaline earth metal salts such as calcium, magnesium salts, aluminum salts, salts with organic bases such as ammonia, methylamine, diethylamine, ethanolamine, dicyclohexylamine, N-methylmorpholine, N-methyl-D-glucamine, and salts with amino acids such as arginine and lysine. Basic nitrogen-containing groups can be quaternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The terms "therapeutically acceptable salt," and "pharmaceutically acceptable salt," as used herein, represent both salts and zwitterionic forms of the compounds of the present invention which are water or oil-soluble or dispersible; which are suitable for treatment of diseases without undue toxicity, irritation, and allergic response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzene sulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethane sulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reacting a carboxyl, phenol or similar group with a suitable base such as a metal hydroxide, carbonate, or bicarbonate, or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

In some embodiments, the thiazolide compound may be administered as a part of a pharmaceutical composition. The pharmaceutical composition may include in addition to the thiazolide compound may include a carrier, such as a pharmaceutically acceptable carrier. The term "carrier" may be used in its broadest sense. For example, the term "carrier" refers to any carriers, diluents, excipients, wetting agents, buffering agents, suspending agents, lubricating agents, adjuvants, vehicles, delivery systems, emulsifiers, disintegrants, absorbents, preservatives, surfactants, colorants, flavorants, and sweeteners. In some embodiments, the carrier may be a pharmaceutically acceptable carrier, a term narrower than carrier, because the term pharmaceutically acceptable carrier" means a non-toxic that would be suitable for use in a pharmaceutical composition. Actual dosage levels of active ingredients in the pharmaceutical compositions may vary so as to administer an amount of the active compound(s) that is effective to achieve the desired therapeutic response for a particular patient.

The selected dose level may depend on the activity of the thiazolide compound, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient may depend on a variety of factors, including the body weight, general health, diet, time and route of administration and combination with other therapeutic agents and the severity of the condition or disease being treated.

The pharmaceutical compositions may be administered systemically, for example, in an oral formulation, such as a solid oral formulation. For example, it may be in the physical form of a powder, tablet, capsule, lozenge, gel, solution, suspension, syrup, or the like. In some embodiments, the pharmaceutical composition may be in a form of a formulation disclosed in U.S. Pat. Nos. 8,524,278 and 9,351,937. Such formulation may, for example, include a controlled release portion, which includes a thiazolide compound, such as nitazoxanide and/or tizoxanide; and an immediate release portion, which contains a thiazolide compound, such as nitazoxanide and/or tizoxanide. These compositions may be administered in a single dose or in multiple doses which are administered at different times.

In some embodiments, the total amount of a thiazolide compound, such as nitazoxanide and/or tizoxanide, in the composition may be about 60% to 75% by weight of the composition. The composition may be formulated for immediate release, controlled release or sustained release. The compositions may contain one or more additional pharmaceutically acceptable additives or excipients. These excipients are therapeutically inert ingredients that are well known and appreciated in the art. As used herein, the term "inert ingredient" may refer to those therapeutically inert ingredients that are well known in the art of pharmaceutical manufacturing, which can be used singly or in various combinations, and include, for example, diluents, disintegrants, binders, suspending agents, glidants, lubricants, fillers, coating agents, solubilizing agent, sweetening agents, coloring agents, flavoring agents, and antioxidants. See, for example, Remington: The Science and Practice of Pharmacy 1995, edited by E. W. Martin, Mack Publishing Company, 19th edition, Easton, Pa.

Examples of diluents or fillers include, but are not limited to, starch, lactose, xylitol, sorbitol, confectioner's sugar, compressible sugar, dextrates, dextrin, dextrose, fructose, lactitol, mannitol, sucrose, talc, microcrystalline cellulose, calcium carbonate, calcium phosphate dibasic or tribasic, dicalcium phosphaste dehydrate, calcium sulfate, and the like. The amount of diluents or fillers may be in a range between about 2% to about 15% by weight of the entire composition. Examples of disintegrants include, but are not limited to, alginic acid, methacrylic acid DVB, cross-linked PVP, microcrystalline cellulose, sodium croscarmellose, crospovidone, polacrilin potassium, sodium starch glycolate, starch, including corn or maize starch, pregelatinized starch and the like. Disintegrant(s) typically represent about 2% to about 15% by weight of the entire composition.

Examples of binders include, but are not limited to, starches such as potato starch, wheat starch, corn starch; microcrystalline cellulose; celluloses such as hydroxypropyl cellulose, hydroxyethyl cellulose, hydroxypropylmethyl cellulose (HPMC), ethyl cellulose, sodium carboxy methyl cellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, and the like. The amount of binder(s) is about 0.2% to about 14% by weight of the entire composition.

Examples of glidants include, but are not limited to, silicon dioxide, colloidal anhydrous silica, magnesium trisilicate, tribasic calcium phosphate, calcium silicate, magnesium silicate, colloidal silicon dioxide, powdered cellulose, starch, talc, and the like. The amount of glidant(s) is about 0.01% to about 0.3% by weight of the entire composition.

Examples of lubricants include, but are not limited to, magnesium stearate, aluminum stearate, calcium stearate, zinc stearate, stearic acid, polyethylene glycol, glyceryl behenate, mineral oil, sodium stearyl fumarate, talc, hydrogenated vegetable oil and the like. The amount of lubricant(s) is about 0.2% to about 1.0% by weight of the entire composition. The compositions may contain a binder that is a low-viscosity polymer. Examples of low-viscosity polymers include, but are not limited to, low-viscosity hydroxypropyl methylcellulose polymers such as those sold by Dow Chemical under the tradename "MethoceL™" (e.g., Methocel E50LV™, Methocel K100LVR™, and Methocel F50LVR™) and low-viscosity hydroxyethylcellulose polymers. The low-viscosity polymer is typically present at about 10% to about 20%, or about 10% to about 15%, or preferably about 12%, of the total weight of the entire composition, or, in those embodiments having controlled release and immediate release portions, the low-viscosity polymer in the controlled release portion is typically present at about 15% to about 20%, preferably about 18%, of the weight of the controlled release portion. The compositions may further comprise a coating material. The coating material is typically present as an outer layer on the dosage form that completely covers the formulation. For example, in some embodiments, the dosage form is an oral tablet in which the controlled release portion forms a first layer of the tablet and the immediate release portion forms a second layer that is deposited on top of the first layer to form a core tablet. In such embodiments, e.g., the coating material can be in the form of an outer coating layer that is deposited on top of the core tablet. The coating material typically is about 1% to about 5% by weight of the composition, and may comprise hydroxypropylmethylcellulose and/or polyethylene glycol, and one or more excipients selected from the group comprising coating agents, opacifiers, taste-masking agents, fillers, polishing agents, coloring agents, antitacking agents and the like. Examples of film-coating substances and methods for using such coating substances are well known to those of skill in the art. The composition comprising a thiazolide compound, such as nitazoxanide and/or tizoxanide, may be administered for a length of time suitable to effectively treat a disease or condition caused by or associated with a virus belonging to the Picornaviridae family, such as a virus belonging to the *Enterovirus* genus, or a virus belonging to the Paramyxoviridae family. A number of appropriate dosages and regimen may be used for the compositions. In some embodiments, administration may be carried out over a period of about 3 days to about 104 weeks. In some embodiments, administration may be carried out over a period longer than 104 weeks and may even be carried out indefinitely. Appropriate regimens may be determined by a physician.

In some embodiments, administering of a thiazolide compound, such as such as nitazoxanide and/or tizoxanide, may start within 24 hours or within 36 hours or within 48 hours or within 60 hours or within 72 hours or within 96 hours from an onset in a patient, such as a human being, of at least one symptom of a disease or condition caused by or associated with a virus belonging to the Picornaviridae family, such as a virus belonging to the *Enterovirus* genus, or with a virus belonging to the Paramyxoviridae family. For example, for a virus belonging to the *Enterovirus* genus, administering of a thiazolide compound, such as such as nitazoxanide and/or tizoxanide, may start within 24 hours or within 36 hours or within 48 hours or within 60 hours or within 72 hours or within 96 hours from an onset in a patient, such as a human being, of at least one symptom of a disease or condition caused by or associated with such virus, which may be, for example, fever, cough, sore throat, nasal obstruction, fatigue, headache, myalgia, and feverishness.

In some embodiments, a daily dose of a thiazolide compound, such as nitazoxanide and/or tizoxanide, administered to a human may be from 100 mg to 1300 mg or from 200 mg to 1200 mg or from 250 mg to 1100 mg or from 300 mg to 1000 mg or any dose value or subrange within these ranges. Exemplary dosage values include 100 mg, 200 mg, 300 mg, 400 mg, 500 mg, 600 mg, 700 mg or 800 mg.

In some embodiments, a thiazolide compound, such as nitazoxanide and/or tizoxanide, may be administered at least for 2 days or at least for 3 days or at least for 4 days or at least for 5 days or at least for 6 days. In some embodiments, a thiazolide compound, such as nitazoxanide and/or tizoxanide, may be administered for a period from 2 to 14 days or from 3 to 10 days or from 4 to 7 days or any value or subrange within these ranges. In certain embodiments, a thiazolide compound, such as nitazoxanide and/or tizoxanide, may be administered for 5 days. The dose of the thiazolide compound, such as nitazoxanide and/or tizoxanide, may be from 300 mg to 900 mg or from 400 mg to 800 mg or from 500 mg to 700 mg or any dose value or subrange within these ranges. Exemplary dosage values include 300 mg, 400 mg, 500 mg, 600 mg, 700 mg or 800 mg. The thiazolide compound, such as nitazoxanide and/or tizoxanide, may be administered once, twice or thrice daily. In certain cases, 600 mg of nitazoxanide and/or tizoxanide may be administered twice daily. The thiazolide compound, such as nitazoxanide and/or tizoxanide, may be co-administered with a direct-acting antiviral agent, against Picornaviridae, such as rupintrivir or MK-0608 or a direct-acting antiviral agent against respiratory syncytial virus such as the fusion inhibitor, GS-5806. A dose of the direct-acting antiviral agent may vary. The direct-acting antiviral agent, such as rupintrivir, MK-0608 or GS-5806, may be co-administered once, twice or thrice daily. In certain cases, 600 mg of nitazoxanide and/or tizoxanide may be administered twice daily together with an effective amount of the direct-acting antiviral administered twice daily.

A thiazolide compound may be administered to a subject affected by a virus belonging to the Picornaviridae family, such as a virus belonging to the *Enterovirus* genus, or a virus belonging to the Paramyxoviridae family. Such subject may be an animal, including a human being.

Preferably, a thiazolide compound, such as nitazoxanide and/or tizoxanide is administered to a subject affected by a virus belonging to the Picornaviridae family, such as a virus belonging to the *Enterovirus* genus, or to a subject affected by a virus belonging to the Paramyxoviridae family in an effective amount, which may mean an amount necessary to achieve a desired effect. Embodiments described herein are further illustrated by, though in no way limited to, the following working examples.

EXAMPLES

The Paramyxoviridae family comprises many important human viral pathogens, including measles, mumps, parainfluenza, RSV (respiratory syncytial virus), *metapneumoviruses* and *henipaviruses*, which cause some of the deadliest emerging zoonoses. The lack of an effective antiviral therapy underscores the need for novel drugs effective against these viruses. It was shown previously that nitazoxanide (NTZ), a safe, orally bioavailable thiazolide licensed in the USA for treating *Cryptosporidium parvum* and *Giardia lamblia* infections, has antiviral activity against influenza viruses. Herein we investigated the activity of NTZ and a class of second-generation thiazolides (SGT), RM-4848 and RM-5038 against Paramyxoviridae infection in vitro, using Sendai virus (SeV) and RSV-A2 as models, and explored the mechanism of the antiviral action. Virus yield was determined by hemagglutinin titration and infectivity assay in monkey and human cells; cell viability was determined by MTT assay. Viral protein synthesis/maturation was characterized by SDS/PAGE-autoradiography after [$^{35}$S]methionine-labeling, immunoprecipitation and/or EndoH-digestion, and by immunofluorescence and Western-blot analysis in infected cells or in cells transiently transfected with FLAG-tagged Hendra virus (HeV) fusion (F) protein.

NTZ and SGT showed a remarkable antiviral activity against SeV, reducing virus yield dose-dependently with SI ranging from >50 to >625 depending on the m.o.i., and protecting host cells from virus-induced damage. Thiazolides did not affect virus entry nor caused a general inhibition of viral protein synthesis whereas they inhibited the maturation and intracellular translocation of the viral HN and F glycoproteins. In particular, NTZ also caused a decrease in intracellular levels of the F protein, which plays a critical role in cell fusion and infectivity of the virion. This effect was not due to protein degradation via the ubiquitin-proteasome system or autophagy, since it could not be rescued by treatment with the proteasome inhibitor bortezomib or autophagy inhibitor chloroquine. Instead SeV F protein was found to be present in an insoluble state in NTZ-treated cells, suggesting that a drug-induced defect in maturation would lead to F protein aggregation. Interestingly, thiazolides similarly affected Hendra virus F protein in cells transiently expressing FLAG-tagged HeV-F in the absence of viral infection, suggesting a cell-mediated mechanism. The results indicate that NTZ is effective against *Paramyxovirus* infection, acting at post-entry level by a novel mechanism targeting viral glycoproteins. NTZ treatment was also effective against RSV, suggesting a general effect of the drug on Paramyxoviridae family members. Results of the study presented in FIGS. 4-19.

Materials and Methods

Cell Culture, Treatment and Transfections. Human A549 alveolar type II-like epithelial cells and cervical carcinoma HeLa cells, and African green monkey kidney cells (AGMK, 37RC cell line) were grown at 37° C. in a 5% $CO_2$ atmosphere in RPMI medium (Gibco-Invitrogen, Carlsbad, Calif.) (AGMK, A549), or DMEM medium (Gibco-Invitrogen, Carlsbad, Calif.) (HeLa), supplemented with 10% fetal calf serum (FCS), 2 mM glutamine and antibiotics. Nitazoxanide (NTZ), tizoxanide (TIZ) (Romark Laboratories, L.C.), glycosylation inhibitor tunicamycin (TM), proteasome inhibitor bortezomib and autophagy inhibitor chloroquine, (Sigma-Aldrich, St. Louis, Mo.) dissolved in DMSO stock solution (25 mg/ml) were diluted in culture medium and added to infected cells immediately after a one-hour adsorption period, unless differently specified. Compounds were maintained in the medium for the duration of the experiment. Controls received equal amounts of DMSO vehicle, which did not affect cell viability or virus replication. Each concentration of each compound was tested in duplicate and each experiment was repeated at least twice. For transfection experiments, semiconfluent monolayers of HeLa cells were transiently transfected with a pCMV-driven construct containing the gene expressing the F protein of human respiratory syncytial virus (RSV, subtype A, strain A2) linked to a FLAG-tag (RSV-F ORF C-Flag tag, Sino Biological Inc.), a pCMV-driven construct containing the gene expressing the F protein of Hendra virus (HeV) linked to a FLAG-tag (HeV-F ORF C-Flag tag, Sino Biological Inc.), or the pcDNA3 vector as control. Transfections were performed using jetPRIME Transfection Reagent (Polyplus transfection), according to the manufacturer's instructions.

Cytotoxicity. Cell viability was determined by the 3-(4,5-dimethylthiazol-2-yl)-2,5-diphenyltetrazolium bromide (MTT) to MTT formazan conversion assay (Sigma-Aldrich, St Louis, Mo.). For MTT assay, reduced MTT (formazan) was extracted from cells by adding 100 ml of acidic isopropanol containing 10% Triton X-100, and formazan absorbance was measured in an ELISA microplate reader at two different wavelengths (540 and 690 nm). The 50% lethal dose ($LD_{50}$) was calculated using Prism 5.0 software (Graph-Pad Software Inc., San Diego, Calif.). Microscopical examination of mock-infected or virus-infected cells was performed daily to detect virus-induced cytopathic effect and possible morphological changes and/or cytoprotection induced by the drug. Microscopy studies were performed using a Leica DM-IL microscope and images were captured on a Leica DC 300 camera using Leica Image-Manager500 software. Virus Preparation, Infection and Titration. Sendai virus (SeV) was grown in the allantoic cavity of 10-day-old embryonated eggs. After 48 h at 37° C., the allantoic fluid was harvested and centrifuged at 5,000 rpm for 30 minutes to remove cellular debris, and virus titers were determined by hemagglutinin (HA) titration and plaque assay, according to standard procedures (Bernasconi et al., 2005, Pica et al., 2000).

For virus infection, confluent AGMK cell monolayers were infected with SeV for 1 hour at 37° C. at a multiplicity of infection (MOI) of 3 PFU (Plaque Forming Unit)/cell, unless differently specified. Similar conditions were utilized for infection of human A549 cells. After the adsorption period, the viral inoculum was removed, and cell monolayers were washed three times with phosphate-buffered saline (PBS). The cells were maintained at 37° C. in RPMI 1640 culture medium containing 2% fetal calf serum. For multi-step virus growth curves, confluent AGMK/A549 cell monolayers were infected with SeV for 1 h at 37° C. at an MOI of 0.01 PFU/cell. After the 1 h adsorption period, the viral inoculum was removed, and cell monolayers were washed three times with PBS. Cells were maintained at 37° C. in RPMI 1640 culture medium containing 0.5% bovine serum albumin (BSA) and L-1-tosylamide-2-phenylethyl chloromethyl ketone (TPCK)-treated trypsin (1 µg/ml) (Sigma-Aldrich). Virus yield was determined 24 and 48 h post infection (p.i.) by HA titration or by plaque assay, as previously described (Rossignol et al., 2009). For the plaque assay, serial 10-fold dilutions of the virus were prepared and inoculated on confluent AGMK cell monolayers in 35-mm plates (Corning, New York, N.Y.). After 1 h at 37° C., the inoculum was removed and the cells were washed three times with PBS before the addition of RPMI containing 0.5% BSA, 1 µg/ml TPCK-treated trypsin, and 0.5% SeaPlaque agarose (Lonza). After 72 h at 37° C., the overlay was removed and cells were fixed with 4% paraformaldehyde in PBS and stained with 1% crystal violet (Sigma-Aldrich). The $IC_{50}$ (50% inhibitory concentration) and $IC_{90}$ (90% inhibitory concentration) of the antiviral compounds was calculated using Prism 5.0 software.

Human pneumovirus RSV-A2 (respiratory syncytial virus, A2 strain) was provided by Dr. G. Toms, University of Newcastle, Newcastle upon Tyne, UK. For RSV infection, confluent HeLa cell monolayers were infected for 1 h at 37° C. with RSV-A2 at an MOI of 1 $TCID_{50}$ (50% tissue culture infective dose)/cell. RSV-A2 yield was evaluated by counting the number of virus-induced syncytia at 48 hours p.i., as determined by immunofluorescence (IF) analysis after labeling with a monoclonal antibody specific for the fusion protein (F protein) of RSV (anti-F 1E3 antibody, Viratom Ltd., Newcastle upon Tyne, UK). For IF analysis, uninfected and RSV-infected HeLa cell monolayers were fixed with 4% paraformaldheyde (4% in PBS) for 30 min at room temperature. Fixed cells were incubated with the anti-F 1E3 antibody for 1 h at room temperature. Unbound antibody was removed by rinsing in PBS, followed by incubation with FITC-conjugated antimouse antibody for 1 h at room temperature. After staining, cells were examined in a Leica DM-I1 fluorescence microscope equipped with UV excitation filters. The images were captured with a Leica DC-300 camera using Leica Image-Manager500 software. At least 150 syncytia were counted for each samples. Nitazoxanide was found to possess antiviral activity against RSV-A2 at non cytotoxic doses, with an $IC_{50}$ of 0.3 µg/ml and an $IC_{90}$ of 0.8 µg/ml.

Metabolic Labeling, Analysis of Protein Synthesis and Western Blot. Mock-infected or virus-infected cells were labeled with 10 µCi/ml of [$^{35}$S]-methionine-cysteine ([$^{35}$S]-Met/Cys, Redivue Pro-Mix $^{35}$S in vitro cell-labeling mix; GE Healthcare) for the indicated times after 30 minutes starvation in methionine/cysteine-free medium. [$^{35}$S]-Met/Cys incorporation was determined after cell lysis in RIPA (radioimmune precipitation assay) buffer (150 mM NaCl, 10 mM Tris-HCl pH 7.5, 4 mM EDTA, 1% Triton X-100, 600 mM KCl), containing 1 mM phenylmethylsulphonyl fluoride (PMSF) and a protease inhibitor mixture (PIC; Roche Applied Science, Penzberg, Germany). Samples containing the same amount of radioactivity or the same amount of protein were separated by SDS/PAGE (3% stacking gel, 10% resolving gel) and processed for autoradiography, as described (Pica et al., 2000). Autoradiographic patterns were visualized and quantified in Typhoon-8600 Imager [(Molecular Dynamics Phosphor-Imager™ (MDP)], and images were acquired using ImageQuant software (Amersham Pharmacia Biotech) (MDP analysis).

For analysis of soluble/insoluble proteins whole-cell extracts (WCE) were prepared after lysis in high-salt extraction buffer (Buffer B) (50 mM Tris-HCl pH 7.5, 400 mM NaCl, 1 mM EDTA, 1 mM EGTA, 1% Triton X-100, 0.5% NP-40 and 10% glycerol) supplemented with 2 mM dithiothreitol (DTT), 20 mM β-glycerolphosphate, 19 mM (p-Nitrophenyl Phosphate) PNPP, 2 mM $Na_3VO_4$, 1 mM PMSF and protease-inhibitors cocktail (Roche) (Rossi et al., 2000). Briefly, cells were washed twice with ice-cold PBS and then lysed in Buffer-B (80 µl). After one cycle of freeze and thaw, and centrifugation at 15,000 rpm (15 min at 4° C.), supernatant (soluble) and pellet (insoluble) fractions were collected. Insoluble fractions were solubilized in 60 µl of Buffer-S (50 mM Tris-HCl pH 8.5, 1% SDS and protease inhibitors) by sonication on ice, using an ultrasonic UP50H processor (Hielscher) (40% amplitude, pulse mode: 6×10 sec, 15 sec pauses). Total extracts were obtained by lysing cells in Laemmli Buffer followed by DNA shearing through a 28½-gauge insulin syringe 10 times.

For Western blot analysis, cell extracts (25 µg) were separated by SDS-PAGE and blotted to nitrocellulose, and filters were incubated with the following antibodies: monoclonal anti-SeV-F ($\alpha$F-$\gamma$236; ID Pharma) and anti-$\alpha$-tubulin (B-5-1-2, Sigma-Aldrich) antibodies; polyclonal anti-$\alpha$-tubulin (11H10; Cell Signaling Technology Inc.), anti-FLAG (DYKDDDDK Tag, Cell Signaling Technology, Inc.) and anti-$\beta$-actin (Sigma-Aldrich) antibodies, followed by decoration with peroxidase-labeled anti-rabbit IgG, anti-goat IgG or anti-mouse IgG (SuperSignal detection kit; Pierce).

Immunofluorescence Microscopy. SeV-infected AGMK or A549 cells and RSV-F- or HeV-F-transfected HeLa cells grown on coverslips were fixed with 4% paraformaldehyde in PBS for 20 minutes at room temperature at 24 h p.i. Mock-infected or mock-transfected cells were processed similarly. Fixed cells were either incubated with anti-F monoclonal antibodies (aF-$\gamma$236; ID Pharma) or anti-FLAG (DYKDDDDK Tag, Cell Signaling Technology, Inc.) polyclonal antibodies for 1 h at 37° C. for plasma membrane staining, or were permeabilized with 0.1% TritonX-100-PBS for 10 minutes at room temperature and then incubated with monoclonal anti-F and anti-calnexin (Stressgene) or polyclonal anti-$\alpha$-tubulin (11H10; Cell Signaling Technology Inc.) antibodies for 1 h at 37° C., followed by decoration with Alexa Fluor488-conjugated (Molecular Probes-Invitrogen) or rhodamine-conjugated (Pierce) goat anti-mouse IgG, and rhodamine-conjugated goat anti-rabbit IgG (Pierce). The nuclei were stained with 4',6-diamidino-2-phenylindole (DAPI) or Hoechst 33342 (Molecular Probes, Invitrogen). The images were captured with an Olympus Fluoview FV-1000 confocal laser scanning system, using FluoView-1000 software.

Statistical Analysis. Statistical analysis was performed using Student's t test for unpaired data. The data are expressed as the means±S.D. of duplicate samples. p values of <0.05 were considered significant.

REFERENCES

Bernasconi, D., Amici, C., La Frazia, S., Ianaro, A., and Santoro, M. G. (2005) *J. Biol. Chem.* 280, 24127-24134.

La Frazia, S., Amici, C., and Santoro, M. G. (2006) *Antivir. Ther.* 11, 995-1004.

Pica, F., Palamara, A. T., Rossi, A., De Marco, A., Amici, C., and Santoro, M. G. (2000) *Antimicrob. Agents Chemother.* 44, 200-204.

Rossi, A., Kapahi, P., Natoli, G., Takahashi, T., Chen, Y., Karin, M., and Santoro, M. G. (2000) *Nature* 403, 103-108.

Rossignol, J. F., La Frazia, S., Chiappa, L., Ciucci, A., Santoro, M. G. (2009) *J. Biol. Chem.* 284, 29798-29808.

Study RM08-3002 (Clinical Trial Data for Enterovirus/Rhinovirus)

A randomized trial conducted in the United States, Canada, Belgium, Australia and New Zealand studied the effect of NTZ, oseltamivir (OST), NTZ+OST and placebo on time to alleviation of symptoms in subjects 13 to 65 years of age with uncomplicated influenza or influenza-like illness. 1,941 subjects with fever, at least one moderate or severe respiratory symptom (cough, sore throat, nasal obstruction), and at least one moderate or severe constitutional symptom (feverishness, headache, myalgia, fatigue, cough, nasal obstruction and sore throat) were enrolled within 48 hours of symptom onset. Nasopharyngeal swabs were collected at baseline and subjected to viral culture and RT-PCR to identify viral causes of illness.

After enrollment, patients were randomly assigned to receive treatment with nitazoxanide extended release tablets (NTZ), oseltamivir capsules (OST), NTZ+OST, or placebo. Each treatment was administered twice daily for 5 days. The NTZ dose was 600 mg, and the OST dose was 75 mg.

Patients recorded the severity of their symptoms twice daily for at least 14 days as either absent, mild, moderate or severe, and symptoms were considered alleviated when all symptoms were graded as absent or mild and remained so for at least 24 hours without the use of symptom relief medications. The primary endpoint of the study was time from first dose to the alleviation of symptoms.

Figure 2:
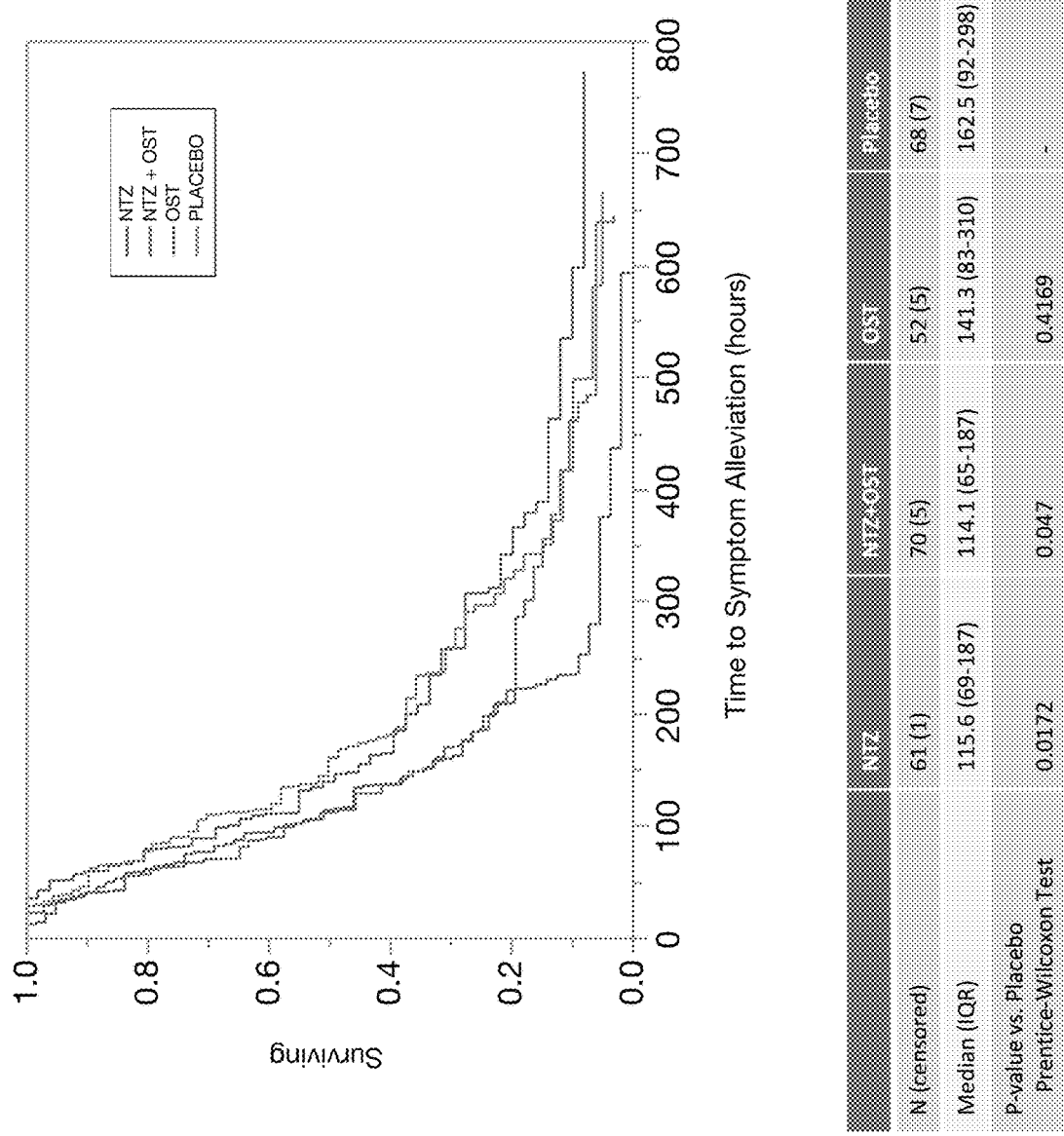
FIG. 2 is a Kaplan-Meier survival chart for patients infected with a virus belonging to the *Enterovirus* genus (including *enteroviruses* and *rhinoviruses*) identified as their sole cause of illness and treated with a) nitazoxanide; b) nitazoxanide and oseltamivir; c) oseltamivir and d) placebo.

Based upon RT-PCR assays (Luminex NxTAG Respiratory Pathogen Panel) of nasopharyngeal swab samples, 251 subjects had viruses from the Enterovirus genus (including enteroviruses and rhinoviruses) identified as their sole cause of illness. The times to symptom alleviation for these patients are plotted in a Kaplan-Meier survival analysis chart presented in FIG. 2.

Both treatment groups that received NTZ showed statistically significant ($p<0.05$) reductions in time to alleviation of symptoms compared to patients receiving placebo. The median reduction of time to symptom alleviation compared to placebo was approximately 47 hours.

Figure 3:
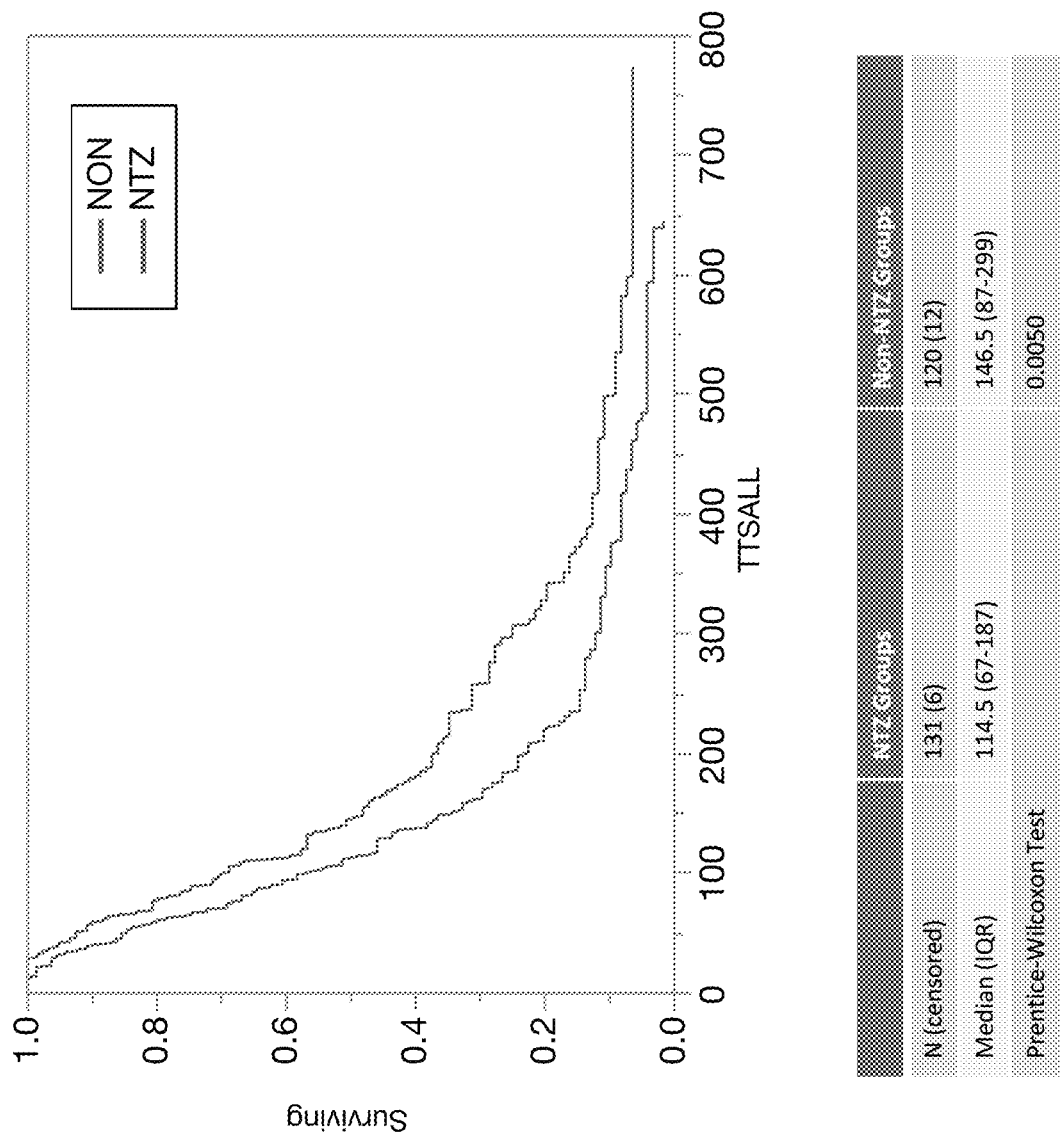
FIG. 3 is a Kaplan-Meier survival chart for patients infected with a virus belonging to the *Enterovirus* genus (including *enteroviruses* and *rhinoviruses*) identified as their sole cause of illness and treated with a) nitazoxanide per se or a combination of nitazoxanide and oseltamivir and b) oseltamivir per se or placebo.
Figure 4:
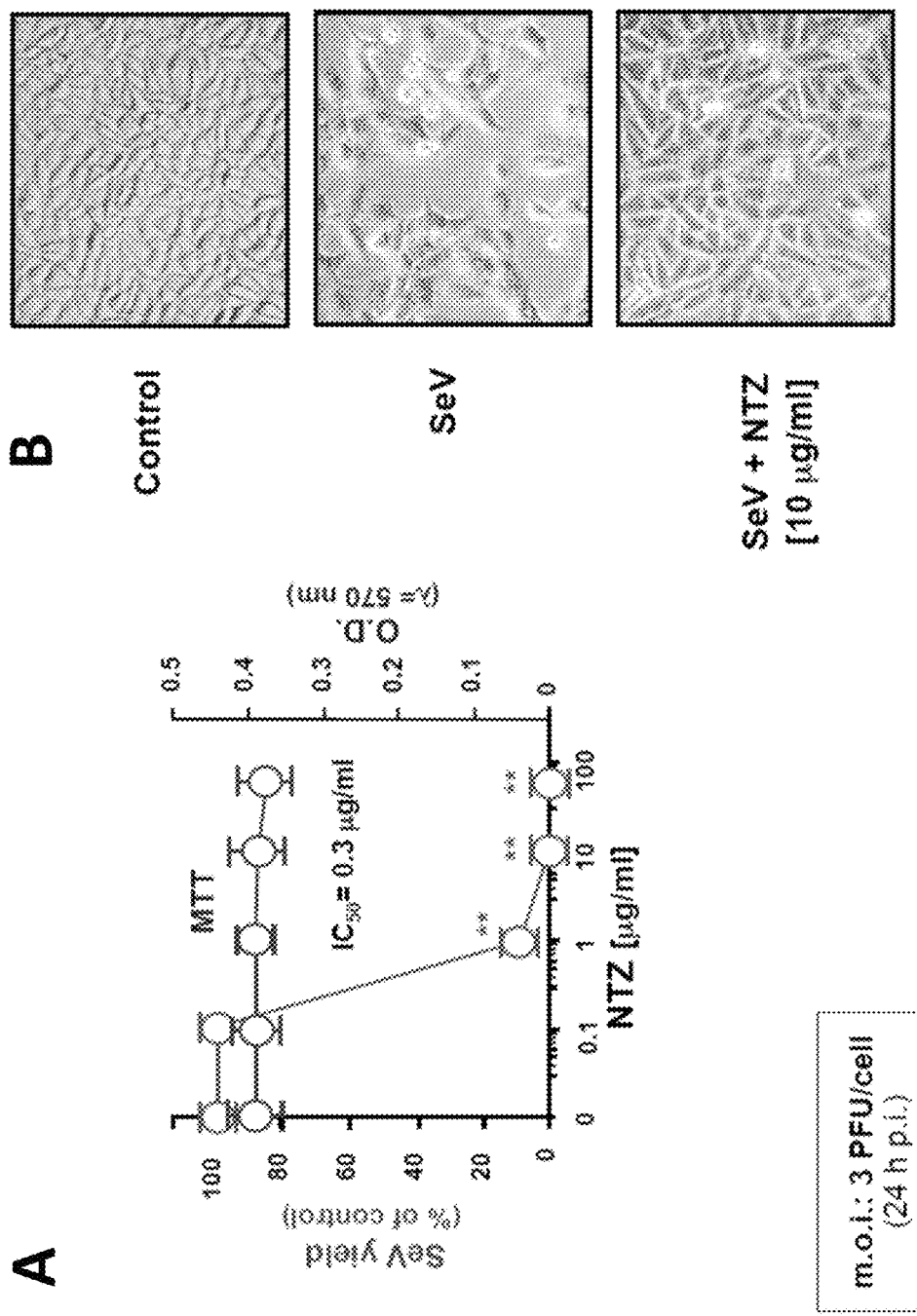
FIG. 4A-B illustrate antiviral activity of nitazoxanide in Sendai virus infected AGMK cells. In particular.

When the two groups receiving NTZ were combined and compared to the two groups that did not receive NTZ (OST and placebo), patients receiving NTZ showed significant ($p=0.005$) reductions in the times to symptom alleviation for patients receiving NTZ compared to those that did not. The results of this comparison are presented in FIG. 3.

Figure 1:
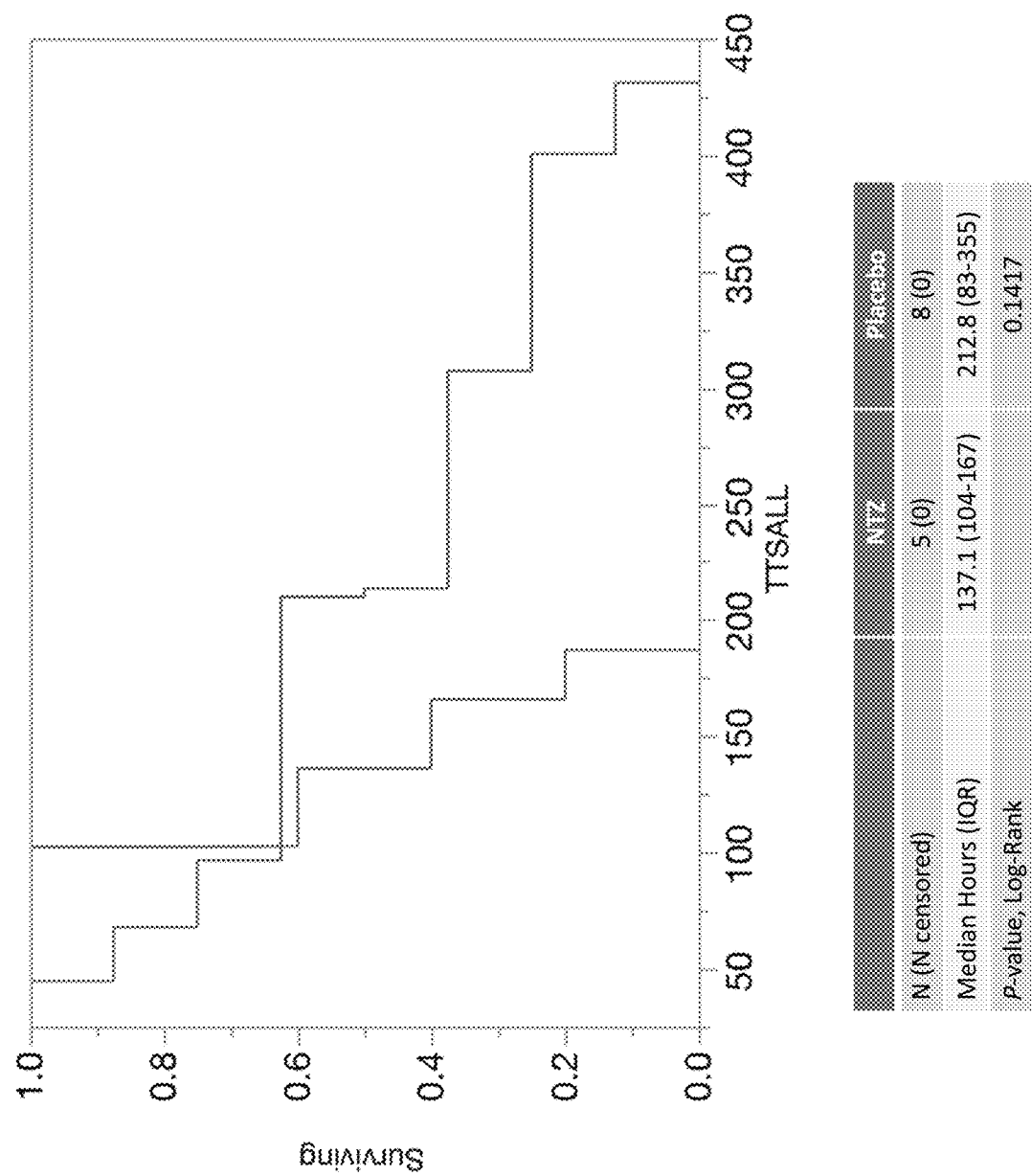
FIG. 1 is a Kaplan-Meier survival analysis chart for respiratory syncytial virus (RSV) infected patients treated with nitazoxanide and placebo. TTSALL stands for Time to Symptom Alleviation (hours). This plot shows that treatment with nitazoxanide was associated with a 76 hour reduction in duration of symptoms at the median.

Based upon RT-PCR assays (Luminex NxTAG Respiratory Pathogen Panel) of nasopharyngeal swab samples, 13 patients had respiratory syncytial virus identified as their sole cause of illness. The times to alleviation of symptoms, such as feverishness, headache, myalgia, fatigue, cough, nasal obstruction and sore throat, for these patients are plotted in a Kaplan-Meier survival analysis chart presented in FIG. 1.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of reducing a duration of symptoms of a disease or condition having as a sole cause of the disease or condition, Rhinovirus A, comprising administering to a subject in need thereof 500 mg to 700 mg of a thiazolide compound selected from nitazoxanide, tizoxanide and a combination thereof or a pharmaceutically acceptable salt thereof as a monotherapy, wherein the subject has at least one symptom of the disease or condition, said at least one symptom being selected from a fever, feverishness, headache, myalgia, fatigue, cough, nasal obstruction and sore throat, wherein said administering provides a reduction of a duration of the at least one symptom in the subject compared to an average duration of the at least one symptom in an untreated patient population of the disease or condition, wherein the disease or condition has a symptom duration defined by the average duration of the at least one symptom in the untreated patient population.

2. The method of claim 1, wherein the at least one symptom comprises at least one moderate or severe respiratory symptom selected from cough, sore throat, and nasal obstruction.

3. The method of claim 1, wherein the at least one symptom comprises:
   a fever, at least one moderate or severe respiratory symptom selected from cough, sore throat, and nasal obstruction, and at least one moderate or severe constitutional symptom selected from headache, myalgia, and fatigue.

4. The method of claim 1, wherein the average duration of the at least one symptom in the untreated patient population is from 92 hours to 298 hours.

5. The method of claim 2, wherein the average duration of the at least one symptom in the untreated patient population is from 92 hours to 298 hours.

6. The method of claim 3, wherein the average duration of the at least one symptom in the untreated patient population is from 92 hours to 298 hours.

7. The method of claim 1, wherein the subject is a human being.

8. A method of treating a disease or condition having as a sole cause of the disease or condition, Rhinovirus A, comprising administering to a subject in need thereof 500 mg to 700 mg of a thiazolide compound selected from nitazoxanide, tizoxanide and a combination thereof or a pharmaceutically acceptable salt thereof as a monotherapy, wherein the subject has at least one respiratory symptom of the disease or condition, said at least one respiratory symptom being selected from cough, nasal obstruction and sore throat.

9. The method of claim 8, wherein the subject has symptoms of the disease or condition, said symptoms comprise (a) a fever, (b) at least one moderate or severe respiratory symptom selected from cough, sore throat, and nasal obstruction, and (c) at least one moderate or severe constitutional symptom selected from headache, myalgia, and fatigue.

10. The method of claim 8, wherein the subject is a human being.

* * * * *